(12) United States Patent
Iwawaki et al.

(10) Patent No.: US 10,828,378 B2
(45) Date of Patent: Nov. 10, 2020

(54) NUCLEIC ACID CONSTRUCT FOR EXPRESSION OF OXIDATIVE STRESS INDICATOR AND USE THEREOF

(75) Inventors: Takao Iwawaki, Saitama (JP); Daisuke Oikawa, Saitama (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 13/980,811

(22) PCT Filed: Jan. 20, 2012

(86) PCT No.: PCT/JP2012/051738
§ 371 (c)(1),
(2), (4) Date: Jul. 19, 2013

(87) PCT Pub. No.: WO2012/099279
PCT Pub. Date: Jul. 26, 2012

(65) Prior Publication Data
US 2013/0298263 A1      Nov. 7, 2013

(30) Foreign Application Priority Data
Jan. 21, 2011   (JP) ................. 2011-010833

(51) Int. Cl.
| | | |
|---|---|---|
| A61K 49/00 | (2006.01) | |
| C07K 14/82 | (2006.01) | |
| G01N 21/359 | (2014.01) | |
| C07K 14/47 | (2006.01) | |
| A01K 67/027 | (2006.01) | |
| G01N 33/50 | (2006.01) | |

(52) U.S. Cl.
CPC ...... *A61K 49/0008* (2013.01); *A01K 67/0275* (2013.01); *C07K 14/4702* (2013.01); *C07K 14/82* (2013.01); *G01N 21/359* (2013.01); *G01N 33/5008* (2013.01); *A01K 2217/052* (2013.01); *A01K 2227/105* (2013.01); *A01K 2267/0393* (2013.01); *G01N 2800/7009* (2013.01)

(58) Field of Classification Search
CPC ............. G01N 21/359; G01N 33/5008; G01N 2800/7009; A01K 67/0275; A01K 2217/052; A01K 2227/105; A01K 2267/0393; C07K 14/4702; C07K 14/82; A61K 49/0008
See application file for complete search history.

(56) References Cited

U.S. PATENT DOCUMENTS

| | | |
|---|---|---|
| 6,179,928 B1 | 1/2001 | Carlton |
| 7,595,375 B2 | 9/2009 | Miyawaki |
| 7,981,637 B2 | 7/2011 | Miyawaki |
| 7,981,658 B2 | 7/2011 | Miyawaki |
| 7,993,879 B2 | 8/2011 | Tsein |
| 8,013,119 B2 | 9/2011 | Nagai |
| 2003/0022198 A1 | 1/2003 | Kaelin et al. |
| 2006/0003961 A1 | 1/2006 | Semenza |
| 2011/0206615 A1 | 8/2011 | Miyawaki et al. |

FOREIGN PATENT DOCUMENTS

| | | |
|---|---|---|
| CN | 101948805 A | 1/2011 |
| EP | 1 867 716 A1 | 12/2007 |
| JP | 2005-095171 | 4/2005 |
| WO | WO-2004/020458 A2 | 3/2004 |
| WO | WO 2005/049790 A2 | 6/2005 |
| WO | WO-2010/010672 A1 | 1/2010 |

OTHER PUBLICATIONS

Kwak et al 2002, Mol. Cell. Biol. 22:2883-2892.*
McMahon et al 2004, J. Biol. Chem. 279: 31556-31567.*
Hurtilla et al 2008, Gene Therapy 15:1271-1279.*
Itoh et al., 2003, Genes to Cells 8:379-391.*
Andrew Tsourkas et al., "Detection of Peroxidase/HO-Mediated Oxidation with Enhanced Yellow Fluorescent Protein", Analytical Chemistry, 2005, 77 (9), 2862-2867.
Bex, Claudia et al., "A yeast two-hybrid system reconstituting substrate recognition of the von Hippel-Lindau tumor suppressor protein", Nucleic Acids Research, Dec. 2007, vol. 35, No. 21, XP-002677873.
De Felipe, P. et al., "E unum pluribus: multiple proteins from a self-processing polyprotein", Trends in Biotechnology, Feb. 1, 2006, vol. 24, No. 2, Elsevier Publications, Cambridge, GB.
EP 09 71 4536.1 Supplementary European Search Report, dated Jul. 9, 2012.
Harada, H. et al. "The combination of hypoxia-response enhancers and an oxygen-dependent proteolytic motif enables real-time imaging of absolute HIF-1 activity in tumor xenografts", Biochemical and Biophysical Research Communications, 2007, vol. 360, pp. 791-796.
International Search Report PCT/JP2009/054236 dated Apr. 28, 2009.
Itoh, K. et al. "An Nrf2/Small Maf Heterodimer Mediates the Induction of Phase II Detoxifying Enzyme Genes through Antioxidant Response Elements", Biochemical and Biophysical Research Communications, 1997, vol. 236, pp. 313-322.

(Continued)

*Primary Examiner* — Maria G Leavitt
*Assistant Examiner* — Kimberly A. Aron
(74) *Attorney, Agent, or Firm* — Foley & Lardner LLP

(57) ABSTRACT

The present invention provides a nucleic acid construct for expressing an oxidative stress indicator comprising: a nucleic acid sequence encoding an Nrf2 protein-derived partial protein that comprises at least an Neh2 domain sequence and substantially lacks or is functionally deficient in an Neh1 domain sequence or an Neh1-Neh3 domain sequence; a stress-inducible promoter sequence positioned upstream of the nucleic acid sequence encoding an Nrf2 protein-derived partial protein; and a nucleic acid sequence encoding a protein capable of generating a detectable signal, the nucleic acid sequence being positioned downstream of the nucleic acid sequence encoding an Nrf2 protein-derived partial protein. The present invention also provides a method for measuring oxidative stress and a method for screening for an anti-oxidative stress agent, using the nucleic acid construct.

13 Claims, 11 Drawing Sheets

Specification includes a Sequence Listing.

(56) References Cited

OTHER PUBLICATIONS

Itoh, K. et al. "Keap1 regulates both cytoplasmic-nuclear shuttling and degradation of Nrf2 in response to electrophiles", Genes to Cells, 2003, vol. 8, pp. 379-391.
Itoh, K. et al. "Keap1 represses nuclear activation of antioxidant responsive elements by Nrf2 through binding to the amino-terminal Neh2 domain", Genes Dev., 1999, vol. 13, pp. 76-86.
John S. Schneekloth et al., "Chemical Genetic Control of Protein Levels: Selective in Vivo Targeted Degradation", Journal of the Americal Chemical Society, 2004, 126 (12), 3748-3754.
Johnson, D. et al. "Activation of the antioxidant response element in primary cortical neuronal cultures derived from transgenic reporter mice", Journal of Neurochemistry, 2002, vol. 81, pp. 1233-1241.
Johnson, J. et al. "The Nrf2-ARE Pathway: An Indicator and Modulator of Oxidative Stress in Neurodegeneration", Ann N Y Acad Sci., Dec. 2008, vol. 1147, pp. 61-69.
Katoh, Y., et al. "Evolutionary conserved N-terminal domain of Nrf2 is essential for the Keap1-mediated degradation of the protein by proteasome", Archives of Biochemistry and Biophysics, 2005, vol. 433, pp. 342-350.
Kobayashi A., et al. "Oxidative Stress Sensor Keap1 Functions as an Adaptor for Cul3-Based E3 Ligase to Regulate Proteasomal Degradation of Nrf2", Molecular and Cellular Biology, Aug. 2004, vol. 24, No. 16, pp. 7130-7139.
Kristina Lindsten et al., "A transgenic mouse model of the ubiquitin/proteasome system", Nature Biotechnology, vol. 21, No. 8, Aug. 2003, pp. 897-902.
Li, Ying-Ping et al., "Hydrogen peroxide stimulates ubiquitin-conjugating activity and expression of genes for specific E2 and E3 proteins in skeletal muscle myotubes", American Journal of Physiology Cell Physiology, Oct. 2003, pp. C806-C812, vol. 285, No. 4 Part 1, XP002677875.

Motohashi, H. et al. "Nrf2-Keap1 defines a physiologically important stress response mechanism", Trends in Molecular Medicine, Nov. 2004, vol. 10, No. 11, pp. 549-557.
Nagai, et al. "A Variant of Yellow Fluorescent protein with fast and efficient maturation for cell-biologial applications", Nature Biotechnology, Jan. 2002, vol. 20, pp. 87-90.
Office Action in U.S. Appl. No. 12/920,283 dated May 15, 2013.
Office Action in U.S. Appl. No. 12/920,283 dated Nov. 30, 2012.
Rushmore, T. et al. "The Antioxidant Responsive Element", The Journal of Biological Chemistry, vol. 266, No. 18, Issue of Jun. 25, 1991, pp. 11632-11639.
Vsevolod V. Belousov et al., "Genetically encoded fluorescent indicator for intracellular hydrogen peroxide", Nature Methods, vol. 3, No. 4, Apr. 2006, p. 281-286.
Wenge Li et al., "Nrf2 Possesses a Redox-sensitive Nuclear Exporting Signal in the Neh5 Transactivation Domain", Journal of Biological Chemistry, vol. 281, No. 37, 27251-27263.
Yashihiro Miwa, "Visualizing Molecules in Living Mammalian Cells Using Degraton Probes", Seikagaku, 2006, p. 14-2, Abstract.
Zheng, Xiaowei et al., "Cell-type-specific regulation of degradation of hypoxia-inducible factor 1(: Role of subcellular compartmentalization", Molecular and Cellular Biology, Jun. 2006, p. 4628-4641, vol. 26, No. 12, , XP-002677874.
Chinese Office Action dated Apr. 3, 2014, in CN 201280005929.2.
Supplementary European Search Report dated Aug. 25, 2014, in EP 12736230.9.
Miao et al., "Transcriptional Regulation of NF-E2 p45-related Factor (NRF2) Expression by the Aryl Hydrocarbon Receptor-Xenobiotic Response Element Signaling Pathway: Direct Cross-Talk Between Phase I and II Drug-Metabolizing Enzymes," The Journal of Biological Chemistry, Mar. 23, 2005, 280(21):20340-20348.

* cited by examiner

NUCLEIC ACID CONSTRUCT FOR EXPRESSION OF OXIDATIVE STRESS INDICATOR AND USE THEREOF

CROSS-REFERENCE TO RELATED APPLICATIONS

This application is a national phase of PCT/JP2012/051738, filed Jan. 20, 2012, which was published on Jul. 26, 2012, as WO 2012/099279, which claims the benefit of JP Application No. 2011-010833, filed Jan. 21, 2011. The respective contents of these prior applications are incorporated here by reference in their entirety.

TECHNICAL FIELD

The present invention relates to a nucleic acid construct for expressing an oxidative stress indicator. Specifically, the oxidative stress is a stress related to an Nrf2-Keap1 pathway.

The present invention also relates to a method for measuring oxidative stress using the nucleic acid construct.

The present invention further relates to a method for screening for an anti-oxidative stress agent using the nucleic acid construct.

BACKGROUND ART

Oxidative stress refers to an imbalance between the production and scavenging systems of reactive oxygen species in the living body, resulting in an excess of the reactive oxygen species. As this state progresses, nucleic acids, proteins, lipids, and the like constituting the living body are oxidized to damage the living body. Upon exposure to oxidative stress or electrophilic substances, cells work toward body's defense by inducing the expression of antioxidant proteins or phase II detoxification enzymes such as glutathione synthetase or heme oxygenase-1 (HO-1) (Non Patent Literature 1). In a gene expression mechanism induced by oxidative stress, an antioxidant response element (ARE) located upstream of the gene and a transcriptional factor Nrf2 binding thereto play an important role (Non Patent Literatures 2 and 3).

Nrf2, a basic leucine zipper (bZip) transcriptional factor, acts as an important control factor for cellular defense against, for example, oxidative stress, electrophilic stress, toxic compounds, and carcinogens (Non Patent Literatures 3, 4, 5, and 6). Under normal conditions, Nrf2 is rapidly degraded through a ubiquitin-proteasome pathway mediated by the association between Nrf2 and Kelch-like ECH associating protein 1 (Keap1; which is a substrate adaptor protein of a Cul3-based ubiquitin-E3 ligase complex) (Non Patent Literatures 7 to 10). Upon exposure to oxidative stress or electrophilic stress, a plurality of reactive cysteine residues in Keap1 are modified by covalent bonds to enable Nrf2 to escape the Keap1-mediated degradation. As a result, the stabilization and subsequent nuclear translocation of Nrf2 take place. In the nucleus, Nrf2 is dimerized with a member of small Maf family proteins. This complex extensively activates transcription via a cis-acting DNA element known as an antioxidant/electrophile response element (ARE/EpRE) (Non Patent Literatures 2 and 3).

Important evidence shows that the Keap1-Nrf2 system is involved in neurodegenerative diseases such as Alzheimer's disease, Parkinson's disease, Huntington's disease, and amyotrophic lateral sclerosis or ameliorates these diseases in in vitro and in vivo models (Non Patent Literature 11). Recent studies using Nrf2 KO mice also show that the dysfunction of Nrf2 is involved in the pathological conditions of human diseases or Nrf2 may play an important role in human diseases (Non Patent Literatures 12 to 14). In addition, Nrf2 has recently been found to have important functions as a body's defense factor against acute lung disorder and acute inflammation (Non Patent Literature 15).

Oxidative stress or cellular response thereto has previously been studied mainly using cultured cells. Known reporters for monitoring the state of oxidative stress are low sensitive. In general, oxidative stress is detected by the measurement of the expression level of a certain type of protein. Specifically, the expression level of the oxidative stress-inducible transcriptional factor Nrf2 has been measured by Western blot analysis. Alternatively, the expression level of HO-1 induced downstream thereof has been measured by Northern blot analysis. These approaches, however, involve a cell lysis process and may thus rarely identify an organ placed under oxidative stress at the individual level. A reporter that permits the expression of alkaline phosphatase by the action of Nrf2 under the control of a promoter that is induced in an oxidative stress-dependent manner has previously been prepared, but is insufficiently sensitive. Since the reporter protein is not suitable for observation in individuals, analysis has not been conducted at the animal individual level and remained at the cultured cell level (Non Patent Literature 16).

For example, a reporter comprising a stress-inducible promoter and a proteolytic regulation site in combination (Non Patent Literature 17), and a probe reagent for measuring oxidative stress, comprising a fluorescent or luminescent protein, a marker protein, and a regulatory protein (Patent Literature 1) have heretofore been known.

Thus, in vivo studies on oxidative stress will provide information useful in the pathology of oxidative stress-related diseases such as neurodegenerative diseases, cardiovascular diseases, diabetes mellitus, and rheumatoid arthritis, the onset of these diseases, and cellular biology.

PRIOR ART LITERATURE

Patent Literature

Patent Literature 1: International Publication No. WO 2009/1078

Non Patent Literature

Non Patent Literature 1: Rushmore T H et al, J. Biol. Chem. 1990; 265 (24): 14648-14653
Non Patent Literature 2: Rushmore T H et al, J. Biol. Chem. 1991; 266 (18): 11632-11639
Non Patent Literature 3: Itoh K et al, Biochem. Biophys. Res. Commun. 1997; 236: 313-322
Non Patent Literature 4: Moi P et al, Proc. Natl Acad. Sci. USA 1996; 91: 9926-9930
Non Patent Literature 5: Venugopal R et al, Proc. Natl Acad. Sci. USA 1996; 93 (25): 14960-14965
Non Patent Literature 6: Motohashi H et al, Proc. Natl Acad. Sci. USA 2004; 101: 6379-6384
Non Patent Literature 7: Itoh K et al, Genes Dev. 1999; 13 (1): 76-86
Non Patent Literature 8: Itoh K et al, Genes Cells 2003; 8: 379-391
Non Patent Literature 9: Kobayashi A et al, Mol. Cell. Biol. 2004; 24: 7130-7139
Non Patent Literature 10: Katoh Y et al, Arch. Biochem. Biophys. 2005; 433: 342-350

Non Patent Literature 11: Johnson J A et al, Ann. NY Acad. Sci. 2008; 1147: 61-69

Non Patent Literature 12: Yoh K et al. Kidney Int. 2001; 60: 1343-1353

Non Patent Literature 13: Yamamoto T et al. Biochem. Biophys. Res. Commun. 2004; 321: 72-79

Non Patent Literature 14: Ishii Y et al. J. Immunol. 2005; 175: 6968-6975

Non Patent Literature 15: Motohashi H and Yamamoto, Trends Mol. Med. 2004; 10 (11): 549-557

Non Patent Literature 16: Johnson D A et al, J. Neurochem. 2002; 81: 1233-1241

Non Patent Literature 17: Harada H et al, Biochem. Biophys. Res. Commun. 2007; 360: 791-796

SUMMARY OF INVENTION

As mentioned above, oxidative stress is known to be related to various diseases. For this reason, there is a growing demand for the construction of a system capable of monitoring or detecting the state of oxidative stress in cells and living bodies with high sensitivity.

In order to facilitate in vivo analysis on oxidative stress, the present inventors have focused on improvement in signal/noise (S/N) ratio in the detection of stress response during oxidative stress by maintaining at least the function of Nrf2 of being ubiquitinated through the association between its Neh2 domain and Keap1 and by deleting the DNA binding ability of its Neh1 domain or Neh1-Neh3 domain. The present inventors have now found an oxidative stress indicator that can be used even in living cells, and designated the indicator as OKD48 (Keap1-dependent oxidative stress detector, No-48, also called "AJISAI (ARE-Nrf2 jointed stress associated indicator)"). The specificity and sensitivity of an oxidative stress indicator such as OKD48 and the usefulness of a transgenic non-human animal expressing the oxidative stress indicator will be described herein.

Specifically, the present invention encompasses the following aspects:

(1) A nucleic acid construct for expressing an oxidative stress indicator comprising: a nucleic acid sequence encoding an Nrf2 protein-derived partial protein that comprises at least an Neh2 domain sequence and substantially lacks or is functionally deficient in an Neh1 domain sequence or an Neh1-Neh3 domain sequence; a stress-inducible promoter sequence positioned upstream of the nucleic acid sequence encoding an Nrf2 protein-derived partial protein; and a nucleic acid sequence encoding a protein capable of generating a detectable signal (e.g., a luminescent or fluorescent protein or a protein bound with a tag sequence capable of labeling), the nucleic acid sequence being positioned downstream of the nucleic acid sequence encoding an Nrf2 protein-derived partial protein.

(2) The nucleic acid construct according to (1), wherein the partial protein comprises an Nrf2 protein-derived amino acid sequence that substantially lacks an Neh1 domain sequence or an Neh1-Neh3 domain sequence.

(3) The nucleic acid construct according to (1) or (2), wherein the Nrf2 protein is mammal-derived Nrf2.

(4) The nucleic acid construct according to (3), wherein the mammal-derived Nrf2 is human Nrf2 or mouse Nrf2.

(5) The nucleic acid construct according to any of (1) to (4), wherein the partial protein comprises (a) an Neh2 domain sequence consisting of amino acids 1-93 in the amino acid sequence of the Nrf2 protein represented by SEQ ID NO: 1 (human) or SEQ ID NO: 2 (mouse), (b) an amino acid sequence having 80% or higher identity to the Neh2 domain sequence, or (c) an amino acid sequence comprising a deletion, substitution, or addition of one or several amino acids in the Neh2 domain sequence.

(6) The nucleic acid construct according to any of (1) to (4), wherein the partial protein comprises (d) an amino acid sequence comprising an Neh2-Neh6 domain sequence consisting of amino acids 1-433 (human) or amino acids 1-425 (mouse) in the amino acid sequence of the Nrf2 protein represented by SEQ ID NO: 1 (human) or SEQ ID NO: 2 (mouse), (e) an amino acid sequence having 80% or higher identity to the amino acid sequence comprising an Neh2-Neh6 domain sequence, or (f) an amino acid sequence comprising the deletion, substitution, or addition of one or several amino acids in the amino acid sequence comprising an Neh2-Neh6 domain sequence.

(7) The nucleic acid construct according to any of (1) to (6), wherein the stress-inducible promoter consists of an antioxidant responsive element (ARE) or a combination of ARE and a promoter.

(8) The nucleic acid construct according to (7), wherein ARE consists of a plurality of repeats.

(9) The nucleic acid construct according to any of (1) to (8), wherein the nucleic acid construct comprises a tag coding sequence at its 3' end.

(10) The nucleic acid construct according to (9), wherein the tag coding sequence is a Flag tag coding sequence.

(11) A vector comprising a nucleic acid construct according to any of (1) to (10).

(12) A cell comprising a nucleic acid construct according to any of (1) to (10) or a vector according to (11).

(13) A non-human animal comprising a nucleic acid construct according to any of (1) to (10) or a vector according to (11).

(14) The non-human animal according to (13), wherein the non-human animal further comprises a nucleic acid construct for endoplasmic reticulum stress indicator expression or a nucleic acid construct for hypoxic stress indicator expression.

(15) A method for measuring oxidative stress, comprising measuring the intensity of a detectable signal (e.g., a luminescence or fluorescence signal) increased in a cell according to (12) or a non-human animal according to (13) or (14) provided with oxidative stress.

(16) A method for screening for an anti-oxidative stress agent, comprising providing a cell according to (12) or a non-human animal according to (13) or (14) with certain oxidative stress in the presence of a candidate agent and determining that the candidate agent has an anti-oxidative stress ability when the intensity of a detectable signal (e.g., a luminescence or fluorescence signal) is lower than that of a control measured in the absence of the candidate agent.

The indicator of the present invention has the advantages that the indicator allows specific detection of oxidative stress related to an Nrf2-Keap1 pathway in cells or animals and can improve the S/N ratio of stress response detection during oxidative stress.

The present description encompasses the contents described in the specification and/or drawings of Japanese Patent Application No. 2011-010833 from which the present application claims the priority.

BRIEF DESCRIPTION OF DRAWINGS

FIG. 2 shows the amino acid sequence alignment between human Nrf2 and mouse Nrf2.

FIG. 5A shows the specificity of AJISA for oxidative stress. HeLa cells were transfected with the OKD48 construct. Luciferase assay was conducted after treatment for 8 hours or 16 hours in the presence or absence of different stressors (sodium arsenite (ASN), diethyl maleate (DEM), $H_2O_2$, tunicamycin (Tun), thapsigargin (Tg), dithiothreitol (DTT), etoposide (Etp), and thenoyltrifluoroacetone (TTFA)). FIG. 5B shows the protein expression of the OKD48 construct under various stresses. HEK293T cells were transfected with the OKD48 construct and treated for 8 hours in the presence or absence of different stressors. The cell lysates were analyzed by Western blotting using an anti-Luc antibody or an anti-GAPDH antibody. FIG. 5C shows the protein expression of endogenous Nrf2 under various stresses. HeLa cells were treated for 8 hours or 16 hours in the presence or absence of different stressors. Then, the cell lysates were analyzed by Western blotting using an anti-Luc antibody or an anti-GAPDH antibody. FIG. 5D shows the influence of Nrf2 overexpression on OKD48 activity. HeLa cells were transfected with the OKD48 construct and an Nrf2 overexpression vector and treated for 8 hours in the presence or absence of sodium arsenite (ASN), followed by luciferase assay. FIG. 5E shows the influence of Keap1 overexpression on OKD48 activity. HeLa cells were transfected with the OKD48 construct and a Keap1 overexpression vector (full length or truncated amino acids 1-314) and treated for 8 hours in the presence or absence of sodium arsenite (ASN), followed by luciferase assay.

FIG. 6 shows the optimization of a luciferase-fused Nrf2 fragment.

FIG. 7A shows a fluorescence image of the OKD48-Venus construct. HEK293T cells were transfected with the OKD48-Venus construct and then treated for 8 hours in the presence or absence of sodium arsenite (ASN) or diethyl maleate. Their fluorescence images were obtained together with phase-contrast images. FIG. 7B shows fluorescence intensity from the OKD48-Venus construct under various stresses. HEK293T cells were transfected with the OKD48-Venus construct and then treated for 8 hours in the presence or absence of sodium arsenite (ASN), diethyl maleate (DEM), $H_2O_2$, tunicamycin (Tun), thapsigargin (Tg), dithiothreitol (DTT), etoposide (Etp), or thenoyltrifluoroacetone (TTFA). Fluorescence from their cell lysates was measured and normalized for luciferase in the cotransfected cells. In the diagram, n.d. represents not detected. FIG. 7C shows the protein expression of the OKD48-Venus construct under various stresses. HEK293T cells were transfected with the OKD48-Venus construct and treated for 8 hours in the presence or absence of various stressors. Their cell lysates were analyzed by Western blotting using an anti-GFP antibody or an anti-GAPDH antibody.

MODES FOR CARRYING OUT THE INVENTION

Figure 1:
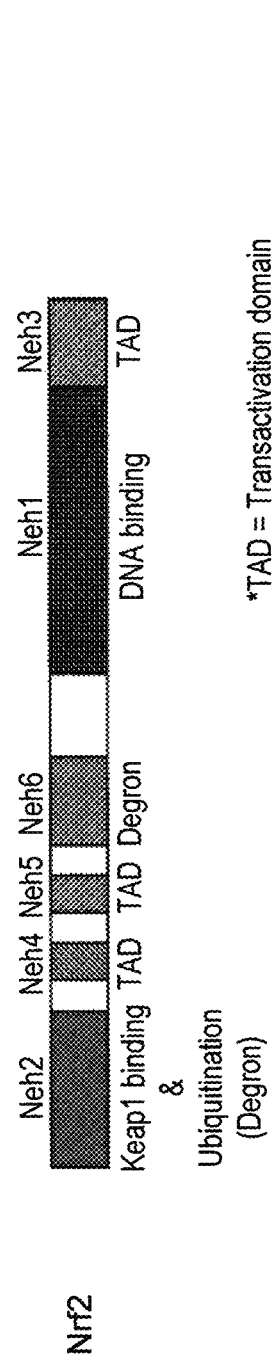
FIG. 1 shows the domain structure of Nrf2 (FIG. 1A) and the position and % identity of each domain in human Nrf2 and mouse Nrf2 (FIG. 1B).

Hereinafter, the present invention will be described in detail.

1. Nucleic Acid Construct for Oxidative Stress Indicator Expression

The nucleic acid construct for expressing an oxidative stress indicator of the present invention comprises: a nucleic acid sequence encoding an Nrf2 protein-derived partial protein that comprises at least an Neh2 domain sequence and substantially lacks or is functionally deficient in an Neh1 domain sequence or an Neh1-Neh3 domain sequence; a stress-inducible promoter sequence positioned upstream of the nucleic acid sequence encoding an Nrf2 protein-derived partial protein; and a nucleic acid sequence encoding a luminescent or fluorescent protein or a protein bound with a tag sequence capable of labeling (using various reagents), the nucleic acid sequence being positioned downstream of the nucleic acid sequence encoding an Nrf2 protein-derived partial protein.

The term "nucleic acid" as used herein is meant to include a gene, DNA, cDNA, RNA, mRNA, chemically modified forms thereof, and the like.

The term "oxidative stress indicator" as used herein is an indicator (an indicator substance or indicator agent) for oxidative stress caused in a cell or in the living body. In the present invention, the oxidative stress indicator refers to an Nrf2 protein that functionally retains at least an Neh2 domain but is functionally deficient in an Neh1 domain or Neh1-Neh3 domains.

The term "functionally retaining an Neh2 domain" used in this context means that the Neh2 domain has an amino acid sequence having 80% or higher, preferably 90% or higher, more preferably 95% or higher identity to the sequence of amino acids 1-93 in the amino acid sequence of SEQ ID NO: 1 (human Nrf2 protein) or SEQ ID NO: 2 (mouse Nrf2 protein), while its function of associating with Keap1 to cause ubiquitination is retained. This function of the Neh2 domain is essential for the Nrf2-mediated degradation of the oxidative stress indicator in a normal state without oxidative stress.

The term "substantially lacking or being functionally deficient in an Neh1 domain or Neh1-Neh3 domains" merely means that "DNA binding ability" as a function of the Neh1 domain is lost. Thus, the Neh1 domain is not necessarily required to be completely deleted. In other words, this term means that a portion, for example, 1 to 50 amino acids, preferably 1 to 20 amino acids, of the Neh1 domain may remain without being deleted. Preferably, the Neh3 domain is absent. In any case, the presence of the Neh1 domain may cause oxidative stress response even in the absence of oxidative stress. Thus, the Neh1 domain has to be rendered unfunctional.

The term "oxidative stress" as used herein refers to an imbalance between the in vivo production and scavenging systems of reactive oxygen species, resulting in an excess of the reactive oxygen species. In the present invention, the oxidative stress is particularly related to the Keap1-Nrf2 pathway. Heme oxygenase-1 (HO-1), which is induced by oxidative stress, is induced by UV-A irradiation, and the Nrf2 protein is known to participate in this induction (Allanson M and Reeve V E, J. Invest. Dermatol. 2004; 122: 1030-1036; and Zhong J L et al. Photochem. Photobiol. Sci. 2010; 9: 18-24). Thus, according to the present invention, even a low level of oxidative stress close to physiological conditions, for example, caused by UV irradiation, can be detected. The intensity of UV irradiation is, for example, 1 to 100 mW/cm$^2$, preferably 2 to 50 mW/cm$^2$, more preferably 5 to 30 mW/cm$^2$. The oxidative stress is related to many diseases such as cardiovascular diseases (e.g., atherosclerosis), neurodegenerative diseases (e.g., Alzheimer's disease, Parkinson's disease, Huntington's disease, and amyotrophic lateral sclerosis), degenerative diseases in each organ (including liver disease), diabetes mellitus, and rheumatoid arthritis. Its relation to inflammatory reaction such as acute or chronic inflammation has also been reported. In the present invention, the oxidative stress can be measured in vitro or in vivo using the oxidative stress indicator.

The term "Nrf2 protein" as used herein refers to a protein that works as a basic leucine zipper (bZip) transcriptional factor inducing, in response to oxidative stress in an animal cell, the expression of an antioxidant protein responsible for the function of protecting the animal cell from the oxidative stress. In a cell free from oxidative stress, Nrf2 is present in a form bound with Keap1 in the cytoplasm. In this state, Keap1 promotes the ubiquitination of Nrf2 through further binding to a ubiquitin ligase complex. Nrf2 thus ubiquitinated is degraded by proteasome, which is a protease complex, so that its function is inhibited. When the cell is exposed to oxidative stress, reactive oxygen reacts with Keap1 to alter its structure. This structural alteration dissociates Keap1 from Nrf2, thereby inhibiting the ubiquitination of Nrf2. As a result, Nrf2 is stabilized without being degraded and thus increases in amount in the cell. Nrf2 translocates into the nucleus where Nrf2 exerts its function as a transcriptional factor. In this process, Nrf2 binds to an antioxidant responsive element (ARE) to cause the expression of oxidative stress defense genes. The oxidative stress defense mechanism mediated by the Nrf2-Keap1 pathway is described in Ken Ito, Biochemistry, 78 (2) pp. 79-92 (2006) (Japan).

As shown in FIG. 1A, Nrf2 is composed of six Nrf2-ECH homology (Neh) domains, i.e., an Neh2 domain, an Neh4 domain, an Neh5 domain, an Neh6 domain, an Neh1 domain, and an Neh3 domain, in this order from the N terminus and highly conserved among species (Ken Ito, 2006, supra). ECH is also known as chicken Nrf2. In this context, Neh2 is a control domain inhibitory to Nrf2 activity and has a Keap1 binding site and a ubiquitination site. Both Neh4 and Neh5 are transactivation domains (TADs) and bind to a transcriptional coactivator (CBP) serving as a cofactor. Neh6 is a domain (degron) that is constantly degraded in the nucleus. Neh1 consists of a basic CNC-specific region (Basic) and a leucine zipper region (L-Zip). The Basic region specifically binds to DNA and participates in nuclear translocation. The L-Zip region is important for heterodimerization with a member of the small Maf family. Neh3 is a region (TAD) that is involved in activation of transcription (Nioi P et al. Mol Cell Biol 2005; 25: 10895-10906).

The term "Neh2-Neh6 domain" as used herein refers to the sequence from the N-terminal amino acid residue of the Neh2 domain to an amino acid residue immediately before the N-terminal amino acid of the Neh1 domain in the Nrf2 protein. The term "Neh1-Neh3 domain" refers to the sequence from the N-terminal amino acid residue of the Neh1 domain to the C-terminal amino acid residue of the Nrf2 protein.

The term "Nrf2" as used herein includes Nrf2 derived from animals such as vertebrates, invertebrates, warm-blooded animals, mammals, and birds, homologs (or orthologs) thereof, and analogs thereof (e.g., variants (which retains the biological activity of Nrf2, but partially includes a deletion, substitution, insertion, or addition of amino acids residue(s)) or chemically modified forms). The amino acid sequence or nucleotide sequence of animal-derived Nrf2 is available by access to a sequence database such as NCBI (GenBank), EMBL, or DDBJ.

Figure 2:
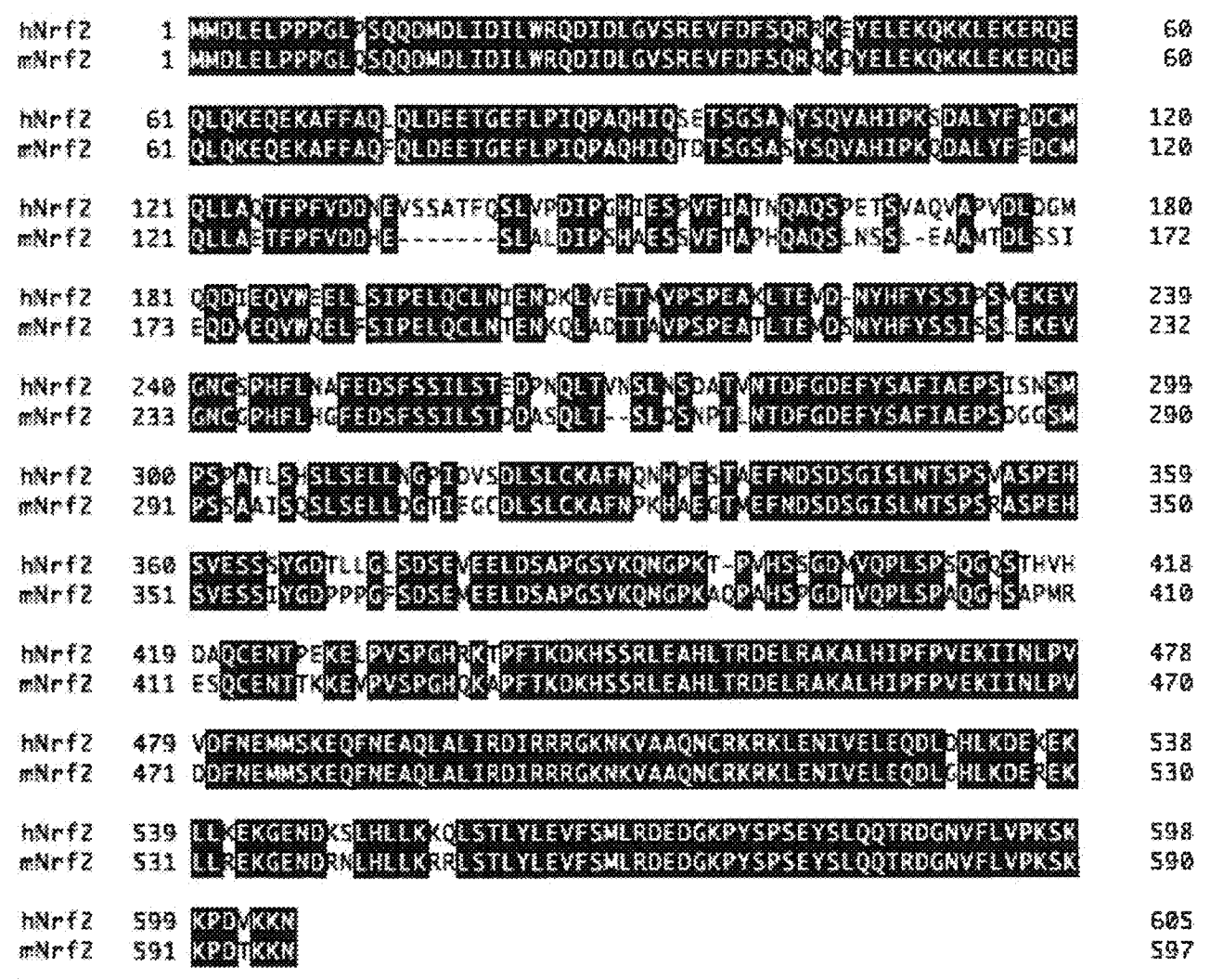

For example, FIG. 2 particularly shows the alignment between the amino acid sequences (SEQ ID NOs: 1 and 2) of human Nrf2 and mouse Nrf2, respectively, among mammal-derived Nrf2 proteins. Human Nrf2 and mouse Nrf2 have approximately 80% sequence identity to each other. FIG. 1B shows the position and % identity of each domain (Neh2, Neh4, Neh5, Neh6, Neh1, and Neh3) in the human and mouse Nrf2 proteins. The sequence identity can be determined using algorithm known in the art such as Basic Local Alignment Search Tool (BLAST) or FASTA (Altschul S F et al, J Mol Biol 215 (3): 403-10, 1990). The % identity means the percentage of the number of identical amino acid residues with respect to the total number of amino acid residues (including the number of gaps) between two amino acid sequences aligned with or without gaps introduced to give the greatest degree of consistency. This definition is also applied to the % identity of the nucleotide sequence of DNA. In this case, nucleotide sequences and nucleotides (or bases) are used instead of the amino acid sequences and the amino acids, respectively.

In the present invention, Nrf2 is preferably mammal-derived Nrf2 as described above, more preferably, for example, human-derived Nrf2 or mouse-derived Nrf2. An Nrf2 region other than the highly conserved domain Neh2 may have a variation (i.e., a deletion, substitution, insertion, or addition) of approximately 20% or less, preferably approximately 10% or less, more preferably approximately 5% or less, for example, approximately 4% or less, approximately 3% or less, approximately 2% or less, or approximately 1% or less of amino acids with respect to the total number of mature amino acid residues. Specifically, the human Nrf2 protein comprises the amino acid sequence represented by SEQ ID NO: 1 or an amino acid sequence having 80% or higher, preferably 90% or higher, more preferably 95% or higher, for example, 96%, 97%, 98%, or 99% or higher identity to the amino acid sequence of SEQ ID NO: 1. On the other hand, the mouse Nrf2 protein comprises the amino acid sequence represented by SEQ ID NO: 2 or an amino acid sequence having 80% or higher, preferably 90% or higher, more preferably 95% or higher, for example, 96%, 97%, 98%, or 99% or higher identity to the amino acid sequence of SEQ ID NO: 2.

The nucleic acid construct of the present invention comprises at least a nucleic acid sequence encoding the indicator and a stress-inducible promoter sequence.

The term "stress-inducible promoter" as used herein refers to a promoter that controls the gene expression of a stress defense gene. Such a promoter includes, for example, but not limited to, quinone reductase (QR) promoters, promoters of genes targeted by Nrf2, an antioxidant responsive element (ARE) which is a promoter activation site, and a Maf-recognition element (MARE). Alternatively, these promoters or promoter activation sites may each be combined with an additional promoter or enhancer. In this context, the additional promoter or enhancer includes virus-derived promoters, mammal-derived promoters, tissue-specific promoters, and the like, and specifically includes, for example, HSV-TK basal promoters (Exp Cell Res. 2009 315 (15): 2496-504), HSV-TK promoters (Cell 1981; 25: 385-398, and Arch. Biol. Sci. Belgrade 2006; 58 (4): 197-203; phRL-TK (Promega Corp.)), cytomegalovirus (CMV) promoters and enhancers (J. Vital. 1995; 69: 2194-2207; pKM2L-pvCMV (RDB No. 5551; RIKEN), pRc/CMV (Invitrogen Corp.), and pCMVTNT (Promega Corp.)), SV-40 virus promoters and enhancers (Cell 1981; 27: 299-308, and J. Virol. 1991; 65 (12): 6900-6912; pKM2L-pvSV40 (RDB No. 5550; RIKEN), pCAT (registered trademark) 3-Enhancer (Promega Corp.), pCAT (registered trademark) 3-Promoter (Promega Corp.), and pGL3-control (Promega Corp.)), and elongation factor-1 (EF-1) promoters (Nucleic Acids Res. 1999; 27 (24); 4775-4782). Examples of the enhancer include enhancers derived from genes targeted by Nrf2, for example, heme oxygenase-1 (HO-1) enhancers (Journal of the Pharmaceutical Society of Japan, 2007; 127 (4): 757-764 (Japan), and Am. J. Physiol. Renal Physiol. 2003; 285: F515-F523), and NAD(P)H dehydrogenase-1 (NQO1) enhancers (Proc Natl Acad Sci USA. 1996; 93: 14960-5). The combination is, for example, a combination of ARE and an HSV-TK basal promoter or a combination of ARE and an HO-1 enhancer, preferably a combination of ARE and an HSV-TK basal promoter.

Specific examples of the sequences of the promoters or the enhancers are shown below.

```
HSV-TK basal promoter (SEQ ID NO: 3):

GGCCCCGCCCAGCGTCTTGTCATTGGCGAATTCGAACACGCAGATGCAGTCGGGG

CGGCGCGGTCCGAGGTCCACTTCGCATATTAAGGTGACGCGTGTGGCCTCGAACA

CCGAGCGACCCTGCAGCGACCCGCTTAACAGCGTCAACAGCG

HSV-TK promoter (phRL-TK (Promega Corp.); nucleotides 543-758) (SEQ ID NO: 4):

CCGTGGCCCGTTGCTCGCGTTTGCTGGCGGTGTCCCCGGAAGAAATATATTTGCAT

GTCTTTAGTTCTATGATGACACAAACCCCGCCCAGCGTCTTGTCATTGGCGAATTC

GAACACGCAGATGCAGTCGGGGCGGCGCGGTCCCAGGTCCACTTCGCATATTAAG

GTGACGCGTGTGGCCTCGAACACCGAGCGACCCTGCAGCGACCCGCTTA

SV40 promoter/enhancer (pGL3-control (Promega Corp.);
nucleotides 48-250) (SEQ ID NO: 5):

TGCATCTCAATTAGTCAGCAACCATAGTCCCGCCCCTAACTCCGCCCATCCCGCCC

CTAACTCCGCCCAGTTCCGCCCATTCTCCGCCCCATCGCTGACTAATTTTTTTTATT

TATGCAGAGGCCGAGGCCGCCTCGGCCTCTGAGCTATTCCAGAAGTAGTGAGGAG

GCTTTTTTGGAGGCCTAGGCTTTTGCAAAAAGCTT

Cytomegalovirus immediate-early enhancer/promoter (pCMVTNT (Promega Corp.);
nucleotides 1-795) (SEQ ID NO: 6):

TCAATATTGGCCATTAGCCATATTATTCATTGGTTATATAGCATAAATCAATATTG

GCTATTGGCCATTGCATACGTTGTATCTATATCATAATATGTACATTTATATTGGC

TCATGTCCAATATGACCGCCATGTTGGCATTGATTATTGACTAGTTATTAATAGTA

ATCAATTACGGGGTCATTAGTTCATAGCCCATATATGGAGTTCCGCGTTACATAAC

TTACGGTAAATGGCCCGCCTGGCTGACCGCCCAACGACCCCCGCCCATFGACGTC

AATAATGACGTATGTTCCCATAGTAACGCCAATAGGGACTTTCCATTGACGTCAA

TGGGTGGAGTATTTACGGTAAACTGCCCACTTGGCAGTACATCAAGTGTATCATA

TGCCAAGTCCGCCCCCTATTGACGTCAATGACGGTAAATGGCCCGCCTGGCATTA

TGCCCAGTACATGACCITACGGGACTTTCCTACTTGGCAGTACATCTACGTATTAG
```

```
TCATCGCTATTACCATGGTGATGCGGTITTGGCAGTACACCAATGGGCGTGGATA

GCGGTTTGACTCACGGGGATTTCCAAGTCTCCACCCCATTGACGTCAATGGGAGTT

TGTTTTGGCACCAAAATCAACGGGACTTTCCAAAATGTCGTAATAACCCCGCCCC

GTTGACGCAAATGGGCGGTAGGCGTGTACGGTGGGAGGTCTATATAAGCAGAGCT

CGTTTAGTGAACCGTCAGATCACTAGAAGCTTTATTGCGGTAGTTTATCACAGTTA

AATTGCTAACGCAGTCAG

Mouse HO-1 enhancer-TK basal promoter (SEQ ID NO: 7):

ACTAGTGAGCTCCACCCCCACCCAGGATTCCAGCCCCCACAGGAGCTGAACTTTGTTTTTCCCGCAGCGGCTGGAATGC
        ├──────▶ HO-1 enhancer

TGAGTTGTGATTTCCTCACTGCTCATTTCCTCAGCTGCTTTTATGCTGTGTCATGGTTGGGAGGGGTGATTAGCAGACAA

AGGGAAGACAGATTTTGCTGAGTCACCCTCTGTTCCCTCTGCCTCAGCTAGGAATAGTTGGTAAAAGGTTCCGGAACGGC

TTTAACTTCAGGCAGAAGGAAGTGAAAGTTCTAGAGGCCCCGCCCAGCGTCTTGTCATTGGCGAATTCGAACACGCAGA
                             ◀──────┤ ├──────▶ TK basal promoter

TGCAGTCGGGGCGGCGCGGTCCGAGGTCCACTTCGCATATTAAGGTGACGCGTGTGGCCTCGAACACCGAGCGACCCTGC

AGCGACCCGCTTAACAGCGTCAACAGCGAAGCTT
                                  ◀──────┤
```

(The sequence indicated in boldface type represents a restriction site; the sequence indicated by "HO-1 enhancer" represents a sequence comprising the HO-1 enhancer; and the sequence indicated by "TK basal promoter" represents a TK basal promoter sequence.)

ARE is a gene expression control sequence (or cis-acting enhancer region) that mediates the induction of the expression of body's defense genes in response to electrophilic substances (e.g., diethyl maleate (DEM), sodium arsenite (ASN), and t-butylhydroquinone (t-BHQ)) causative of oxidative stress. According to an embodiment of the present invention, ARE is a plurality of repeats, preferably 3 to 5 repeats, more preferably 3 repeats. Preferably, such a plurality of repeats involves a spacer sequence consisting of, for example, 1 to 20 arbitrary bases or 1 to 10 arbitrary bases, between the ARE sequence and the ARE sequence. The nucleotide sequence of ARE is TGA(G/C)NNNGC wherein N represents G, C, A, or T (Trends Mol Med. 2004; 10 (11): 549-57), for example, TGACATTGC (SEQ ID NO: 8) and/or TGACAAAGC (SEQ ID NO: 9). A 3-repeat sequence of ARE (3×ARE) used in Examples described later is as follows (SEQ ID NO: 10):

```
ACTAGTGGAAATGACATTGCTAATGGTGACAAAGCAACTTTTCTAGTGGAAATGACATTGCTAATGGTGACAAAGCAAC
        ├──────▶ ARE                ◀──────┤ ├──────▶ ARE                ◀──────

TTTTCTAGTGGAAATGACATTGCTAATGGTGACAAAGCAACTTTTCTAGA
──┤ ├──────▶ ARE                ◀──────┤
```

(The sequence indicated in boldface type represents a restriction site; and the sequence indicated by "ARE" represents a sequence comprising ARE.)

A 3×ARE-TK basal promoter sequence used in Examples described later is as follows (SEQ ID NO: 11):

```
ACTAGTGGAAATGACATTGCTAATGGTGACAAAGCAACTTTTCTAGTGGAAATGACATTGCTAATGGTGACAAAGCAAC
        ├──────▶ ARE                ◀──────┤ ├──────▶ ARE                ◀──────

TTTTCTAGTGGAAATGACATTGCTAATGGTGACAAAGCAACTTTTCTAGAGGCCCCGCCCAGCGTCTTGTCATTGGCGA
──┤ ├──────▶ ARE                ◀──────┤ ├──────▶ TK basal promoter

ATTCGAACACGCAGATGCAGTCGGGGCGGCGCGGTCCGAGGTCCACTTCGCATATTAAGGTGACGCGTGTGGCCTCGAAC

ACCGAGCGACCCTGCAGCGACCCGCTTAACAGCGTCAACAGCGAAGCTT
                                                 ◀──────┤
```

(The sequence indicated in boldface type represents a restriction site; the sequence indicated by "ARE" represents a sequence comprising ARE; and the sequence indicated by "TK basal promoter" represents a TK basal promoter sequence.)

The nucleic acid construct of the present invention can further comprise regulatory sequences such as a terminator, a poly-A sequence, and a ribosomal binding sequence, and, if necessary, a selective marker sequence. The nucleic acid construct may further comprise the 5'-noncoding region sequence and 3'-noncoding region sequence of the Nrf2 gene located upstream and downstream, respectively. This is intended for integration into the cellular genome. The size of the 3'-noncoding region sequence or the 5'-noncoding region sequence is, for example, but not limited to, 1 kb or larger, preferably 1 to 7 kb.

The oxidative stress indicator of the present invention is a modified Nrf2 protein that comprises at least the Neh2 domain of the Nrf2 protein and comprises a luminescent or fluorescent protein or a protein bound with a tag sequence capable of labeling instead of the Neh1 domain or the Neh1-Neh3 domains, preferably the Neh1-Neh3 domains. The nucleic acid construct of the present invention allows observation of luminescence or fluorescence resulting from the expression of the modified Nrf2 protein.

The selective marker sequence is useful for selecting a cell containing the nucleic acid construct of the present invention incorporated therein and can include, for example, drug resistance genes (e.g., a kanamycin resistance gene, an ampicillin resistance gene, and a hygromycin resistance gene). In the case of removing the selective marker sequence after integration into the cellular genome, the selective marker sequence in the nucleic acid construct can be flanked by recombinase recognition sequences (e.g., loxP sequences or FRT sequences) and removed using a recombinase-recombinase recognition sequence system such as a Cre-loxP system or a FLP-FRT system. If necessary, a negative selective marker sequence such as an HSV-TK gene or a diphtheria toxin (DT) gene, or a fragment thereof can be inserted to the nucleic acid construct.

In the present invention, oxidative stress can be detected using an arbitrary protein capable of generating a detectable signal. Also, cells or tissues placed under oxidative stress may be killed specifically using, for example, a cell death-inducing molecule. Preferably, a luminescent or fluorescent protein or a protein bound with a tag sequence capable of labeling is used. Herein, the present invention will also be described with reference to these proteins. However, the present invention is not limited to them.

The luminescent or fluorescent protein used in the present invention is not particularly limited, and any luminescent or fluorescent protein can be used. Examples of the fluorescent protein that can be used include *Aequorea victoria*-derived fluorescent proteins and its derivatives, for example, GFP, YFP, EBFP, ECFP, EGFP, EYFP, and Venus, and coral-derived fluorescent proteins and its derivatives, for example, DsRed, HcRed, and mCherry. Typical examples of the luminescent protein include luciferase, which is a bioluminescence reaction-catalyzing enzyme carried by organisms such as beetles (firefly and click beetle), sea firefly, and bacteria. For the fluorescent protein, see literatures, for example, Shimomura O et al (1962) J Cell Comp Physiol 59: 223-39; Phillips G (2001) FEMS Microbiol Lett 204 (1): 9-18; Shaner N et al (2005) Nat Methods 2: 905-909; and Heim R et al (1995) Nature 373: 663-664. For the luciferase, see literatures, for example, de Wet J R et al (1985) Proc Natl Acad Sci USA 82: 7870-7873, JP Patent Publication (Kokai) No. 2008-289475 A (2008), and JP Patent Publication (Kokai) No. 2005-245457 A (2005). Such a fluorescent or luminescent protein is also commercially available from Clontech Laboratories, Inc., Roche Diagnostics, Chisso Corp. (Japan), etc.

The protein bound with a tag sequence capable of labeling is also called a tag protein and includes, for example, but not limited to, a tetracysteine tag (labeling reagent: FlAsH labeling reagent or ReAsH labeling reagent; Invitrogen Corp.), HaloTag (registered trademark) (labeling reagent: many models; Promega Corp.), SNAP-tag, CLIP-tag, ACP-tag, and MCP-tag (all are labels: many models; New England Biolabs Inc.), and fluorogen activating proteins (FAPs) (Nat. Biotechnol. 2008; 26 (2): 235-240). These tag proteins are proteins labeled by binding with fluorescent tag sequences.

The nucleic acid construct of the present invention can be prepared as shown below. The preparation method shown below is provided merely for illustrative purposes and does not limit the present invention.

The Nrf2 gene derived from animal species (e.g., a human or a mouse) is subjected to cDNA cloning and PCR amplification. The amplification product is incorporated into a vector. Then, the Neh1 coding region or the Neh1-Neh3 coding region of the Nrf2 gene is cleaved off, substantially at both ends, with restriction enzymes. A preliminarily prepared nucleic acid encoding a luminescent or fluorescent protein or a tag protein, or a reporter sequence (e.g., Flag tag)-conjugated luminescent or fluorescent protein or tag protein is inserted to the cleavage site. The Neh1 coding region and the Neh3 coding region correspond to regions encoding, for example, the sequences of amino acids 434-561 and amino acids 562-605, respectively, in the amino acid sequence of SEQ ID NO: 1 in the case of human Nrf2. On the other hand, the Neh1 coding region and the Neh3 coding region correspond to regions encoding, for example, the sequences of amino acids 426-553 and amino acids 554-597, respectively, in the amino acid sequence of SEQ ID NO: 2 in the case of mouse Nrf2 (see FIG. 1B). If this replacement of the Neh1 coding region or the Neh1-Neh3 coding region causes the dysfunction or functional deficiency of the region, a portion, not the whole, of this region, may be replaced with the nucleic acid encoding a luminescent or fluorescent protein or a tag protein. In this case, a nucleic acid encoding the remaining protein portion of the Nrf2 protein from which Neh1 or Neh1-Neh3 has been deleted consists of a nucleic acid encoding an amino acid sequence comprising at least Neh2. The thus-obtained nucleic acid encoding the modified Nrf2 protein is amplified by PCR to recover an amplification product. Since the Neh3 coding region is not necessarily essential, primers designed so as not to amplify this region can be used in the PCR amplification to prepare an amplification product free from the Neh3 coding region. In Examples described later, a nucleic acid encoding hNrf2(1-433)-Luc or mouse Nrf2(1-426)-Luc (wherein Luc represents DNA encoding luciferase) is obtained as an amplification product. These nucleic acid constructs can offer a higher S/N ratio than that by unmodified Nrf2-Luc nucleic acid constructs.

The sequence (3×ARE-TKbasal-OKD48-LUC) actually used in Examples described later is shown below (SEQ ID NO: 12).

```
ACTAGTGGAAATGACATTGCTAATGGTGACAAAGCAACTTTTCTAGTGGAAATGACATTGCTAATGGTGACAAAGCAAC
   |——————> ARE              <——————|    |——————> ARE              <——————|
TTTTCTAGTGGAAATGACATTGCTAATGGTGACAAAGCAACTTTTCTAGAGGCCCCGCCCAGCGTCTTGTCATTGGCGA
 —|    |——————> ARE              <——————|    |——————————————> TK basal promoter
ATTCGAACACGCAGATGCAGTCGGGGCGGCGCGGTCCGAGGTCCACTTCGCATATTAAGGTGACGCGTGTGGCCTCGAAC
ACCGAGCGACCCTGCAGCGACCCGCTTAACAGCGTCAACAGCGAAGCTTCTAGGTACC ATGATGGACTTGGAGCTGCCG
                                                        <——————|
CCGCCGGGACTCCCGTCCCAGCAGGACATGGATTTGATTGACATACTTTGGAGGCAAGATATAGATCTTGGAGTAAGTC
GAGAAGTATTTGACTTCAGTCAGCGACGGAAAGAGTATGAGCTGGAAAAACAGAAAAAACTTGAAAAGGAAAGACAAGA
ACAACTCCAAAAGGAGCAAGAGAAAGCCTTTTTCGCTCAGTTACAACTAGATGAAGAGACAGGTGAATTTCTCCCAATT
CAGCCAGCCCAGCACATCCAGTCAGAAACCAGTGGATCTGCCAACTACTCCCAGGTTGCCCACATTCCCAAATCAGATG
CTTTGTACTTTGATGACTGCATGCAGCTTTTGGCGCAGACATTCCCGTTTGTAGATGACAATGAGGTTTCTTCGGCTAC
GTTTCAGTCACTTGTTCCTGATATTCCCGGTCACATCGAGAGCCCAGTCTTCATTGCTACTAATCAGGCTCAGTCACCT
GAAACTTCTGTTGCTCAGGTAGCCCCTGTTGATTTAGACGGTATGCAACAGGACATTGAGCAAGTTTGGGAGGAGCTAT
TATCCATTCCTGAGTTACAGTGTCTTAATATTGAAAATGACAAGCTGGTTGAGACTACCATGGTTCCAAGTCCAGAAGC
CAAACTGACAGAAGTTGACAATTATCATTTTTACTCATCTATACCCTCAATGGAAAAAGAAGTAGGTAACTGTAGTCCA
CATTTTCTTAATGCTTTTGAGGATTCCTTCAGCAGCATCCTCTCCACAGAAGACCCCAACCAGTTGACAGTGAACTCAT
TAAATTCAGATGCCACAGTCAACACAGATTTTGGTGATGAATTTTATTCTGCTTTCATAGCTGAGCCCAGTATCAGCAA
CAGCATGCCCTCACCTGCTACTTTAAGCCATTCACTCTCTGAACTTCTAAATGGGCCCATTGATGTTTCTGATCTATCA
CTTTGCAAAGCTTTCAACCAAAACCACCCTGAAAGCACAGCAGAATTCAATGATTCTGACTCCGGCATTTCACTAAACA
CAAGTCCCAGTGTGGCATCACCAGAACACTCAGTGGAATCTTCCAGCTATGGAGACACACTACTTGGCCTCAGTGATTC
TGAAGTGGAAGAGCTAGATAGTGCCCCTGGAAGTGTCAAACAGAATGGTCCTAAAACACCAGTACATTCTTCTGGGGAT
ATGGTACAACCCTTGTCACCATCTCAGGGGCAGAGCACTCACGTGCATGATGCCCAATGTGAGAACACACCAGAGAAAG
AATTGCCTGTAAGT CTCGAGGAAGATGCCAAAAACATTAAGAAGGGCCCAGCGCCATTCTACCCACTCGAAGACGGGAC
CGCCGGCGAGCAGCTGCACAAAGCCATGAAGCGCTACGCCCTGGTGCCCGGCACCATCGCCTTTACCGACGCACATATCG
AGGTGGACATTACCTACGCCGAGTACTTCGAGATGAGCGTTCGGCTGGCAGAAGCTATGAAGCGCTATGGGCTGAATACA
AACCATCGGATCGTGGTGTGCAGCGAGAATAGCTTGCAGTTCTTCATGCCCGTGTTGGGTGCCCTGTTCATCGGTGTGGC
TGTGGCCCCAGCTAACGACATCTACAACGAGCGCGAGCTGCTGAACAGCATGGGCATCAGCCAGCCCACCGTCGTATTCG
TGAGCAAGAAAGGGCTGCAAAAGATCCTCAACGTGCAAAAGAAGCTACCGATCATACAAAAGATCATCATCATGGATAGC
AAGACCGACTACCAGGGCTTCCAAAGCATGTACACCTTCGTGACTTCCCATTTGCCACCCGGCTTCAACGAGTACGACTT
CGTGCCCGAGAGCTTCGACCGGGACAAAACCATCGCCCTGATCATGAACAGTAGTGGCAGTACCGGATTGCCCAAGGGCG
TAGCCCTACCGCACCGCACCGCTTGTGTCCGATTCAGTCATGCCCGCGACCCCATCTTCGGCAACCAGATCATCCCCGAC
```

```
ACCGCTATCCTCAGCGTGGTGCCATTTCACCACGGCTTCGGCATGTTCACCACGCTGGGCTACTTGATCTGCGGCTTTCG

GGTCGTGCTCATGTACCGCTTCGAGGAGGAGCTATTCTTGCGCAGCTTGCAAGACTATAAGATTCAATCTGCCCTGCTGG

TGCCCACACTATTTAGCTTCTTCGCTAAGAGCACTCTCATCGACAAGTACGACCTAAGCAACTTGCACGAGATCGCCAGC

GGCGGGGCGCCGCTCAGCAAGGAGGTAGGTGAGGCCGTGGCCAAACGCTTCCACCTACCAGGCATCCGCCAGGGCTACGG

CCTGACAGAAACAACCAGCGCCATTCTGATCACCCCCGAAGGGGACGACAAGCCTGGCGCAGTAGGCAAGGTGGTGCCCT

TCTTCGAGGCTAAGGTGGTGGACTTGGACACCGGTAAGACACTGGGTGTGAACCAGCGCGGCGAGCTGTGCGTCCGTGGC

CCCATGATCATGAGCGGCTACGTTAACAACCCCGAGGCTACAAACGCTCTCATCGACAAGGACGGCTGGCTGCACAGCGG

CGACATCGCCTACTGGGACGAGGACGAGCACTTCTTCATCGTGGACCGGCTGAAGAGCCTGATCAAATACAAGGGCTACC

AGGTAGCCCCAGCCGAACTGGAGAGCATCCTGCTGCAACACCCCAACATCTTCGACGCCGGGGTCGCCGGCCTGCCCGAC

GACGATGCCGGCGAGCTGCCCGCCGCAGTCGTCGTGCTGGAACACGGTAAAACCATGACCGAGAAGGAGATCGTGGACTA

TGTGGCCAGCCAGGTTACAACCGCCAAGAAGCTGCGCGGTGGTGTTGTGTTCGTGGACGAGGTGCCTAAAGGACTGACCG

GCAAGTTGGACGCCCGCAAGATCCGCGAGATTCTCATTAAGGCCAAGAAGGGCGGCAAGATCGCCGTGGACTACAAGGAT

GACGATGACAAGTAATAGCTAGC
```

(The sequence indicated in boldface type represents a restriction site; the sequence indicated by "ARE" represents a sequence comprising ARE; the sequence indicated by "TK basal promoter" represents a sequence comprising the TK basal promoter; the boxed sequence represents an Nrf2 site (aa1-433); the sequence indicated in oblique form represents a Flag tag sequence; and the remaining sequence represents a luciferase sequence (GL4).)

The sequence (3×ARE-TKbasal-OKD48-Venus) actually used in Examples described later is shown below (SEQ ID NO: 13).

```
ACTAGTGGAAATGACATTGCTAATGGTGACAAAGCAACTTTTCTAGTGGAAATGACATTGCTAATGGTGACAAAGCAAC
     |——→ ARE              ←——|    |——→ ARE              ←——

TTTTCTAGTGGAAATGACATTGCTAATGGTGACAAAGCAACTTTTCTAGAGGCCCCGCCCAGCGTCTTGTCATTGGCGA
—|   |——→ ARE                ←——|         |——→ TK basal promoter

ATTCGAACACGCAGATGCAGTCGGGGCGGCGCGGTCCGAGGTCCACTTCGCATATTAAGGTGACGCGTGTGGCCTCGAAC

ACCGAGCGACCCTGCAGCGACCCGCTTAACAGCGTCAACAGCGAAGCTTCTAGGTACC ATGATGGACTTGGAGCTGCCG
                                                    ←——|

CCGCCGGGACTCCCGTCCCAGCAGGACATGGATTTGATTGACATACTTTGGAGGCAAGATATAGATCTTGGAGTAAGTC

GAGAAGTATTTGACTTCAGTCAGCGACGGAAAGAGTATGAGCTGGAAAAACAGAAAAAACTTGAAAAGGAAAGACAAGA

ACAACTCCAAAAGGAGCAAGAGAAAGCCTTTTTCGCTCAGTTACAACTAGATGAAGAGACAGGTGAATTTCTCCCAATT

CAGCCAGCCCAGCACATCCAGTCAGAAACCAGTGGATCTGCCAACTACTCCCAGGTTGCCCACATTCCCAAATCAGATG

CTTTGTACTTTGATGACTGCATGCAGCTTTTGGCGCAGACATTCCCGTTTGTAGATGACAATGAGGTTTCTTCGGCTAC

GTTTCAGTCACTTGTTCCTGATATTCCCGGTCACATCGAGAGCCCAGTCTTCATTGCTACTAATCAGGCTCAGTCACCT

GAAACTTCTGTTGCTCAGGTAGCCCCTGTTGATTTAGACGGTATGCAACAGGACATTGAGCAAGTTTGGGAGGAGCTAT

TATCCATTCCTGAGTTACAGTGTCTTAATATTGAAAATGACAAGCTGGTTGAGACTACCATGGTTCCAAGTCCAGAAGC

CAAACTGACAGAAGTTGACAATTATCATTTTTACTCATCTATACCCTCAATGGAAAAAGAAGTAGGTAACTGTAGTCCA

CATTTTCTTAATGCTTTTGAGGATTCCTTCAGCAGCATCCTCTCCACAGAAGACCCCAACCAGTTGACAGTGAACTCAT

TAAATTCAGATGCCACAGTCAACACAGATTTTGGTGATGAATTTTATTCTGCTTTCATAGCTGAGCCCAGTATCAGCAA
```

```
CAGCATGCCCTCACCTGCTACTTTAAGCCATTCACTCTCTGAACTTCTAAATGGGCCCATTGATGTTTCTGATCTATCA

CTTTGCAAAGCTTTCAACCAAAACCACCCTGAAAGCACAGCAGAATTCAATGATTCTGACTCCGGCATTTCACTAAACA

CAAGTCCCAGTGTGGCATCACCAGAACACTCAGTGGAATCTTCCAGCTATGGAGACACACTACTTGGCCTCAGTGATTC

TGAAGTGGAAGAGCTAGATAGTGCCCCTGGAAGTGTCAAACAGAATGGTCCTAAAACACCAGTACATTCTTCTGGGGAT

ATGGTACAACCCTTGTCACCATCTCAGGGGCAGAGCACTCACGTGCATGATGCCCAATGTGAGAACACACCAGAGAAAG

AATTGCCTGTAAGTCTCGAGGAAGATGCCAAAAACATTAAGAAGGGCCCAGCGCCATTCTACCCACTCGAAGACGGGAC
```

CGACGTAAACGGCCACAAGTTCAGCGTGTCCGGCGAGGGCGAGGGCGATGCCACCTACGGCAAGCTGACCCTGAAGCTGA

TCTGCACCACCGGCAAGCTGCCCGTGCCCTGGCCCACCCTCGTGACCACCCTGGGCTACGGCCTGCAGTGCTTCGCCCGC

TACCCCGACCACATGAAGCAGCACGACTTCTTCAAGTCCGCCATGCCCGAAGGCTACGTCCAGGAGCGCACCATCTTCTT

CAAGGACGACGGCAACTACAAGACCCGCGCCGAGGTGAAGTTCGAGGGCGACACCCTGGTGAACCGCATCGAGCTGAAGG

GCATCGACTTCAAGGAGGACGGCAACATCCTGGGGCACAAGCTGGAGTACAACTACAACAGCCACAACGTCTATATCACC

GCCGACAAGCAGAAGAACGGCATCAAGGCCAACTTCAAGATCCGCCACAACATCGAGGACGGCGGCGTGCAGCTCGCCGA

CCACTACCAGCAGAACACCCCCATCGGCGACGGCCCCGTGTTGCTGCCCGACAACCACTACCTGAGCTACCAGTCCGCCC

TGAGCAAAGACCCCAACGAGAAGCGCGATCACATGGTCCTGCTGGAGTTCGTGACCGCCGCCGGGATCACTCTCGGCATG

GACGAGCTGTACAAGGA*CTACAAGGATGACGA*TGACAAGTAATAGCTAGC (The sequence indicated in boldface type represents a restriction site; the sequence indicated by "ARE" represents a sequence comprising ARE; the sequence indicated by "TK basal promoter" represents a sequence comprising the TK basal promoter; the boxed sequence represents an Nrf2 site (aa1-433); the sequence indicated in oblique form represents a Flag tag sequence; and the remaining sequence represents a Venus sequence (GL4).)

The primers for PCR amplification can be designed on the basis of the nucleotide sequence of the amplification product of interest. Also, routine conditions can be used as PCR conditions.

The PCR reaction generally involves approximately 20 to 45 repetitive cycles each involving the steps of denaturing double-stranded DNA into single DNA strands, annealing primers to the single DNA strands, and elongating the primers with the single DNA strands as templates. The denaturation step consists of, for example, treatment at 94 to 98° C. for approximately 10 seconds to approximately 5 minutes. The annealing step consists of, for example, treatment at approximately 50 to 68° C. for approximately 10 to 60 seconds. The elongation step consists of, for example, treatment at 72° C. for approximately 20 seconds to approximately 10 minutes. Before the start of all the cycles, treatment at 94 to 98° C. for approximately 30 seconds to approximately 5 minutes may be performed. After the completion of all the cycles, treatment at 72° C. for approximately 1 to 10 minutes may be performed. The primers consist of forward and reverse primers and are designed on the basis of the nucleotide sequence of template DNA. The primers are generally 15 to 30 bases, preferably 20 to 25 bases, in size. The PCR reaction solution consists of a PCR buffer containing template DNA, thermostable polymerase, $Mg^{2+}$, dNTPs (N=A, T, C, and G), etc. The PCR reaction can be carried out conveniently using a PCR apparatus such as a thermal cycler. For specific examples of the PCR approach, see, for example, F M Ausubel et al., Short Protocols in Molecular Biology (2002), John Wiley & Sons, R A Siki et al., Science 1985, 230: 1350-1354, and H A Erlich et al., Science 1991, 252: 1643-1651.

Meanwhile, the stress-inducible promoter used as another component in the nucleic acid construct is synthesized or prepared from a library containing the promoter, for example, an animal tissue-derived genomic library, and incorporated into a vector containing a unique restriction site or a multicloning site. In this vector, the nucleic acid encoding the modified Nrf2 protein is inserted in a restriction site or a cloning site located at the 3' side of the stress-inducible promoter. If necessary, the prepared nucleic acid construct is excised from the vector and recovered using a purification method such as electrophoresis. In this context, the stress-inducible promoter is any of those exemplified above, preferably an oxidative stress-inducible promoter. In the present invention, ARE or a combination of ARE and a promoter (e.g., an HSV-TK basal promoter) is preferred. ARE is preferably a plurality of ARE repeats, as mentioned above and is more preferably, for example, 3 repeats of ARE (3×ARE).

Figure 3:
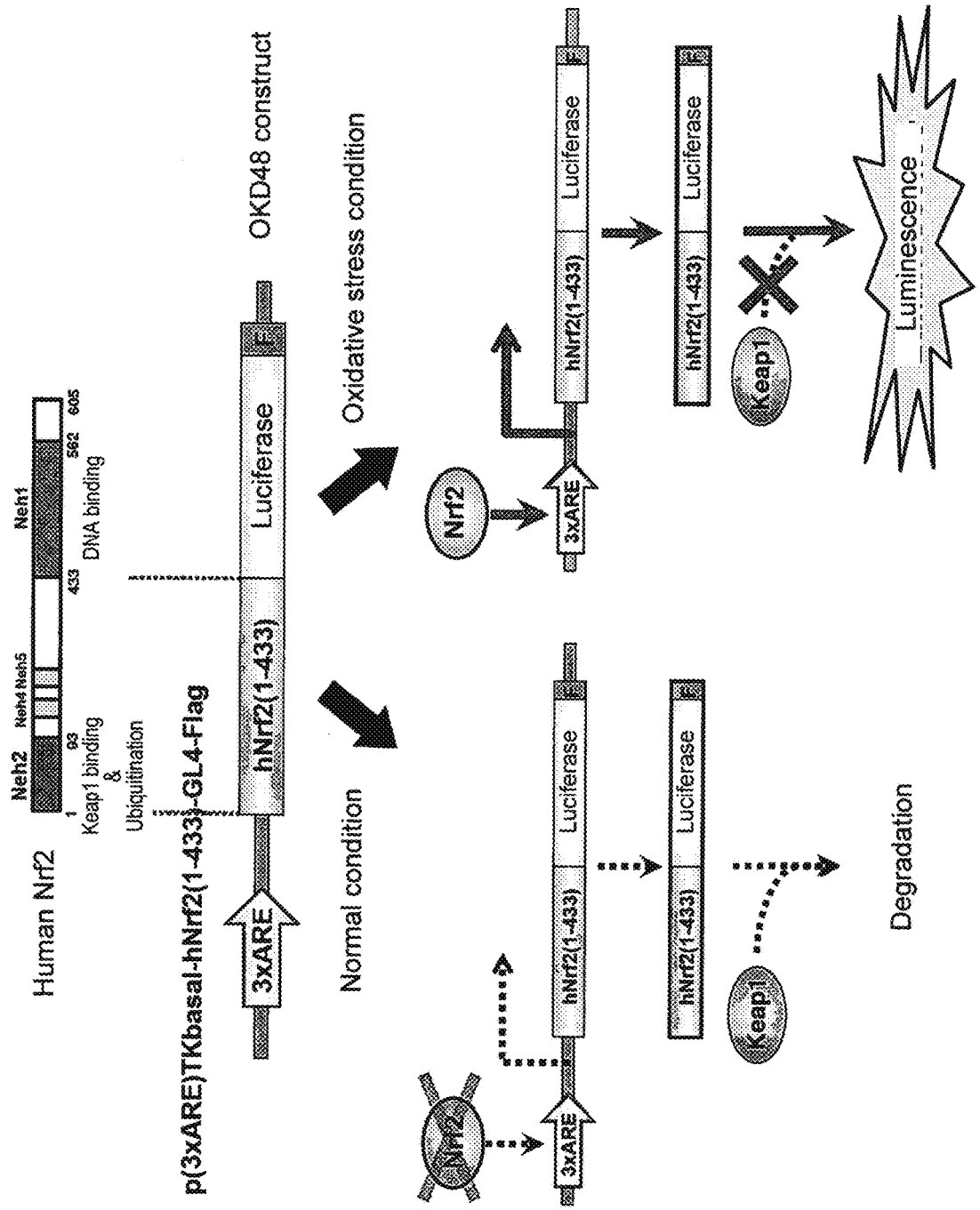
FIG. 3 schematically shows a nucleic acid construct (OKD48) consisting of p(3×ARE)TKbasal-hNrf2(1-433)-GL4-Flag and the inhibition and induction of transcription of the nucleic acid construct under normal conditions and under oxidative stress conditions. p(3×ARE)TKbasal-hNrf2(1-433)GL4-Flag was prepared as the OKD48 construct. In human Nrf2, the Neh2 domain functions as a Keap1 binding and ubiquitination region, and the Neh1 domain functions as a DNA binding region. The OKD48 construct has a 3×ARE promoter, a human Nrf2 (amino acids 1-433) coding sequence, and a Flag-tagged luciferase (GL4) coding sequence. The transcription of the OKD48 construct was not induced under normal conditions. The leaked OKD48 protein was degraded by the Keap1 system. The transcription of the OKD48 construct was induced by the action of the 3×ARE promoter under oxidative stress. The obtained OKD48 protein was stabilized by the Keap1 system. In this way, luminescence was detected only in cells placed under oxidative stress.

In this way, the nucleic acid construct of the present invention as shown in FIG. 3 can be prepared. If this nucleic acid construct is intended for genomic integration, the 5'-noncoding region sequence of approximately 1 to 7 kb and the 3'-noncoding region sequence of approximately 1 to 7 kb of the Nrf2 gene can be ligated with the 5' and 3' ends, respectively, of the nucleic acid construct. A vector comprising such a nucleic acid construct causes homologous recombination with the Nrf2 gene (or Nrf2 gene locus) on the cellular genome. As a result, the nucleic acid construct is integrated into the genome. This approach may be used particularly for preparing a transgenic non-human animal, for example, a transgenic mouse, comprising the nucleic acid construct.

2. Vector

The present invention further provides a vector comprising the nucleic acid construct.

The vector may be any of plasmids (e.g., pBluescript series and pUC series), phages, cosmids, viruses, BAC, PAC, and the like, but not limited to them. The plasmids are plasmids for animal cells, for example, plasmids for mammals. Commercially available plasmids can be used conveniently. The viruses are virus vectors such as adenovirus, adeno-associated virus, retrovirus, hemagglutinating virus of Japan, or lentivirus. BAC and PAC are artificial chromosomes.

Figure 4:
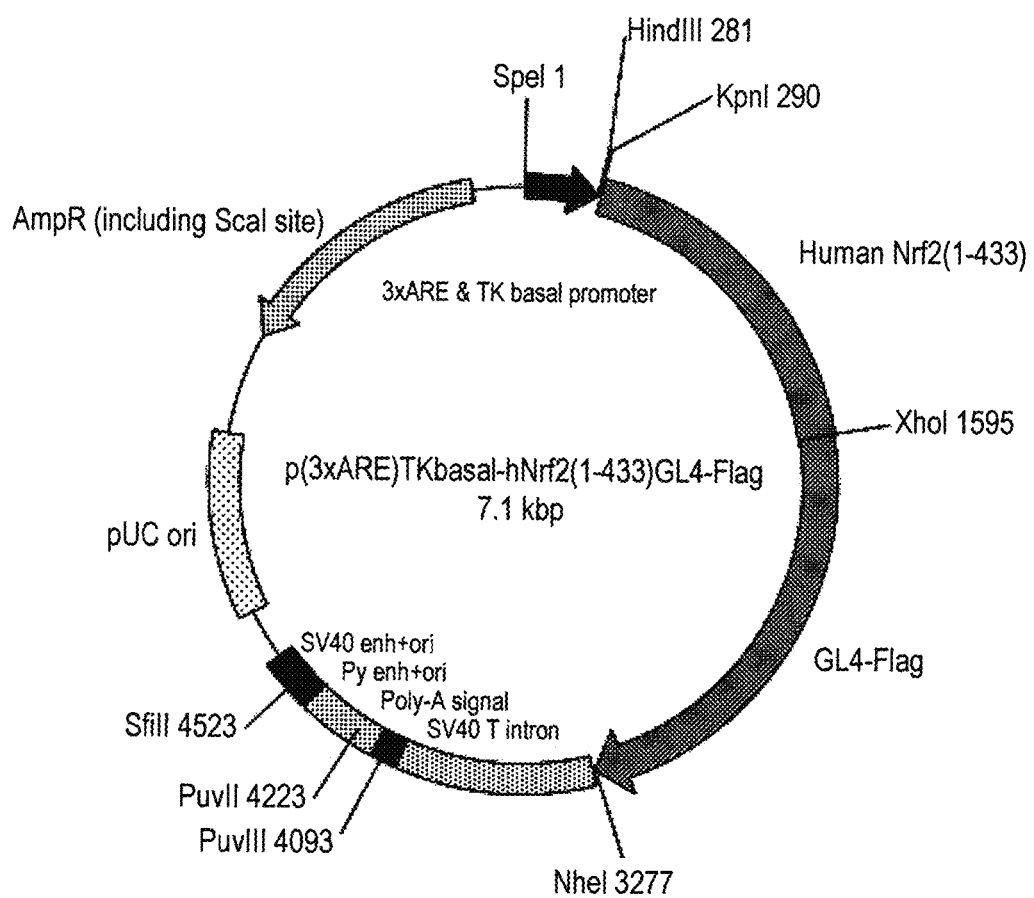
FIG. 4 shows the structure of a vector comprising the nucleic acid construct (OKD48) consisting of p(3×ARE)TKbasal-hNrf2(1-433)-GL4-Flag.

An example of the vector construct of the present invention is shown in FIG. 4.

3. Cell

The present invention further provides a cell comprising the nucleic acid construct or the vector.

The cell is generally an animal cell, preferably a warm-blooded animal cell, more preferably a mammal cell, further preferably a human cell or a mouse cell. The cell also includes, for example, but not limited to, cultured cells, primary cultured cells, subcultured cells, established cell lines, transformed cells, transfected cells, somatic cells, germ cells, embryonic stem (ES) cells, tissue stem cells, cells provided with pluripotent differentiation by gene manipulation or the like (including e.g., induced pluripotent stem (iPS) cells), and cells differentiated from the cells. Examples of the mammal cell include HEK293 cells, CHO cells, BHK cells, COS cells, and HeLa cells.

The cell is transformed or transfected with the nucleic acid construct or the vector of the present invention. The transformation or transfection approach is usually a method for transforming animal cells and includes approaches known in the art, for example, viral infection method, electroporation, microinjection, liposome method, and calcium phosphate method.

The viral infection method is an approach using virus vectors known in the art such as retrovirus, lentivirus, adenovirus, adeno-associated virus, or Sendai virus. This approach utilizes the property of the virus of easily infecting animal cells.

The liposome method is an approach using liposomes such as cationic liposomes, for example, cholesterol-based cationic liposomes. The transformation method using liposomes is also called lipofection. This approach utilizes the anionic electric properties of cell surface. Alternatively, liposomes having surface bound with a cell membrane-permeable peptide (e.g., HIV-1 Tat peptide, penetratin, and oligoarginine peptide) may be used.

4. Non-Human Animal

The present invention further provides a non-human animal comprising the nucleic acid construct or the vector, i.e., a transgenic animal (except for humans), or an offspring animal thereof.

The transgenic animal (except for humans) can be prepared using, for example, nuclear transplantation method or pluripotent cells such as ES cells or iPS cells.

As used herein, the "animal" encompasses, but not limited to, animals except for humans, preferably birds and mammals, for example, primates such as monkeys and chimpanzees, rodents such as mice, rats, and hamsters, artiodactyls useful as livestock animals such as cattle, goats, sheep, and pigs, Carnivora animals such as dogs and cats, and birds such as chickens.

The nuclear transplantation method involves, for example, introducing the nucleic acid construct or the vector of the present invention into the genomes of somatic cells such as fibroblasts, then microinjecting the nuclei taken out of the cells into enucleated fertilized eggs or unfertilized eggs (after electric stimulation in the case of enucleated unfertilized eggs), and transplanting the eggs to the uterus or oviduct of a foster mother, followed by development and delivery to obtain chimeric animals.

The method using ES cells involves introducing the nucleic acid construct or the vector of the present invention to internal cell masses taken out of the blastocysts of animal (except for humans) eggs by an approach such as microinjection, microcell fusion, or electroporation, and then injecting ES cells into blastocysts of recipient embryos to obtain transplant embryos, which are then transplanted to the uterus of a foster mother, followed by delivery to obtain chimeric animals (e.g., Evans M J and Kaufman M H, 1981, Nature 292: 154-156; and Mitsuo Oshimura ed., Chromatin-Chromosome Experimental Protocols (2004), Yodosha Co., Ltd.).

As an example of the method using iPS cells, the nucleic acid construct or the vector is introduced into animal-derived somatic cells in a form capable of expression the nucleic acid encoding the modified Nrf2 protein, to prepare transformed cells. Then, transcriptional factors (e.g., Oct3/4, Sox2, Klf4, and c-Myc) or nucleic acids (including a vector) encoding them are introduced into the cells by an approach described in the literature (e.g., Takahashi K and Yamanaka S 2006, Cell 126: 663-676). The cells are cultured to obtain ES cell-like pluripotent cells. These iPS cells are injected into blastocysts to obtain transplant embryos, which can then be transplanted to the uterus of a foster mother, followed by delivery to obtain chimeric animals. The chimeric animals of interest is screened for by isolating genomic DNA from animal tissues and examining the presence of the introduced nucleic acid by an approach such as Southern hybridization, in situ hybridization, or PCR, or may be determined on the basis of change in the hair color of the animals such as mice.

The chimeric animals thus prepared are further mated with wide-type animals of the same species thereas. The mating of the obtained heterozygous animal individuals can be repeated to obtain homozygous offspring animals (except for humans).

Alternatively, the heterozygous or homozygous offspring animals may be mated with arbitrary animals of the same species thereas to confer an additional feature together with the oxidative stress indicator to the animals. Examples of such arbitrary animals can include, but not limited to, animals of the same species thereas each comprising a nucleic acid construct for endoplasmic reticulum stress indicator expression and animals of the same species thereas each comprising a nucleic acid construct for hypoxic stress indicator expression. Even an offspring animal that results from mating over multiple generations should be understood as the offspring animal according to the present invention as long as the oxidative stress indicator of the present invention functions therein.

For example, the mating with the animal of the same species comprising a nucleic acid construct for endoplasmic reticulum stress indicator expression can produce a non-human animal comprising the nucleic acid construct for oxidative stress indicator expression and the nucleic acid construct for endoplasmic reticulum stress indicator expression. Similarly, the mating with the animal of the same species comprising a nucleic acid construct for hypoxic stress indicator expression can produce a non-human animal comprising the nucleic acid construct for oxidative stress indicator expression and the nucleic acid construct for hypoxic stress indicator expression.

Endoplasmic reticulum stress is related to an IRE1a-XBP1 pathway, an ATF6 pathway, a PERK-ATF4 pathway, and the like and related to neurodegenerative diseases such as Alzheimer's disease, Parkinson's disease, polyglutamine disease, and amyotrophic lateral sclerosis, metabolic diseases such as diabetes mellitus, hyperlipidemia, and obesity, and other diseases such as cancer. The endoplasmic reticulum stress is detected by an endoplasmic reticulum membrane protein such as ATF6, IRE1, or PERK. Since IRE1, for example, induces the splicing of XBP1, a system capable of examining endoplasmic reticulum stress in vivo through the use of this reaction (ERAI system) has been developed. Alternatively, ATF6 is converted to an active form of the ATF6 protein by cleavage, while PERK phosphorylates eIF-2α to cause functional reduction, which in turn promotes the synthesis of ATF4. Thus, their derivatives are used for the analysis of endoplasmic reticulum stress (JP Patent Publication (Kokai) No. 2005-204516 A (2005); and Yoshida H., FEBS J. 2007 Feb.; 274 (3): 630-58. ER stress and diseases.).

Hypoxic stress refers to stress response that is caused when cells are exposed to conditions of lower oxygen concentration than the oxygen concentration at which the cells normally grow. The hypoxic stress is known to be related to, for example, a pathway involving HIF-1α.

The non-human animal comprising a nucleic acid construct for endoplasmic reticulum stress indicator expression is a non-human animal having a nucleic acid construct for endoplasmic reticulum stress indicator expression comprising an XBP1 gene (containing introns) downstream of a promoter (which may be combined with an enhancer, if necessary), and a luminescent or fluorescent protein or tag protein coding sequence linked to the 3' side thereof, or a vector comprising the construct. Examples of the promoter, etc., include, but not limited to, promoters and/or enhancers derived from viruses such as cytomegalovirus (CMV) and SV-40 virus, β-actin promoters, elongation factor-1 (EF-1) promoters, and combinations thereof. The XBP1 gene may be linked, for example, at its 5' end, to a sequence encoding a tag such as Flag.

The nucleic acid construct for endoplasmic reticulum stress indicator expression is, for example, a construct comprising a tag (example of the tag: Flag) coding sequence, an XBP1 gene, and a luminescent or fluorescent protein or tag protein coding sequence, in this order, downstream of a sequence comprising a CMV enhancer and a β-actin promoter.

The nucleotide sequence and amino acid sequence of X-box binding protein 1 (XBP1) are available from GenBank (NCBI, USA), etc., for example, under Accession No. NM_013842 (mouse), NM_00107953, (human), or NM_005080 (human).

The non-human animal of the present invention can also be mated with a non-human animal with the oxidative stress-related disease as described above, for example, an animal (e.g., mouse) model of the disease, to prepare a non-human animal with the disease comprising the nucleic acid construct for oxidative stress indicator expression and, optionally, an additional nucleic acid construct for stress indicator expression such as a nucleic acid construct for endoplasmic reticulum stress indicator expression or a nucleic acid construct for hypoxic stress indicator expression.

The mating with, for example, an AD non-human animal model comprising a chimeric APP gene capable of producing human Aβ as the non-human animal with the oxidative stress-related disease can produce an AD non-human animal model comprising the nucleic acid construct for oxidative stress indicator expression. The same holds true for non-human animal models of other diseases.

Alternatively, a non-human animal comprising the nucleic acid construct for oxidative stress indicator expression and a nucleic acid construct for endoplasmic reticulum stress indicator expression can be mated with an AD non-human animal model comprising a chimeric APP gene capable of producing human Aβ to prepare an AD non-human animal model comprising the nucleic acid construct for oxidative stress indicator expression and the nucleic acid construct for endoplasmic reticulum stress indicator expression. The additional nucleic acid construct for stress indicator expression other than the nucleic acid construct for oxidative stress indicator expression can be selected arbitrarily as shown in the preparation method mentioned above. The same holds true for non-human animal models of other diseases to be mated.

In this way, an animal of the same species (as the original animal) having the oxidative stress indicator and further comprising an additional feature can be prepared arbitrarily as long as it retains the nucleic acid construct for oxidative stress indicator expression.

The non-human animal with the oxidative stress-related disease encompasses, for example, but not limited to, an AD non-human animal model comprising a chimeric APP gene capable of producing human Aβ (JP Patent Publication (Kokai) No. 2008-000027 A (2008)), an AD non-human animal model comprising a human presenilin 2 gene variant (JP Patent Publication (Kokai) No. 11-146743 A (1999)), a Parkinson's disease non-human animal model comprising an α-synuclein gene (WO 2005/041649), a Parkinson's disease non-human animal model comprising a parkin gene variant (JP Patent Publication (Kokai) No. 2003-018992 A (2003)), a diabetes mellitus non-human animal model (Diabetes, 1997 46: 887-894), an obesity non-human animal model (Nature, 372, 425-432, 1994), and a chronic inflammation non-human animal model (Cell Metab, 2009, 10, 178-88).

5. Method for Measuring Oxidative Stress

The present invention further provides a method for measuring the level of oxidative stress, comprising measuring the intensity of a detectable signal (e.g., a luminescence or fluorescence signal) increased in the cell or the non-human animal of the present invention provided with oxidative stress.

In the measurement method of the present invention, for example, a cell or a non-human animal that is free from the nucleic acid construct for oxidative stress indicator expression, a cell or a non-human animal that is not provided with oxidative stress, or a cell or a non-human animal provided with a positive or negative control for oxidative stress can be used as a control for oxidative stress measurement.

In the case of using the cell of the present invention, for example, an oxidative stressor is added to the medium of cultured cells to induce oxidative stress in the cells. Increase in the intensity of intracellular luminescence or fluorescence can be measured using a fluorescence microscope and an imaging apparatus or luciferase assay or fluorescence assay using cell lysates. In addition, the influence of the oxidative stressor on the cells can be observed in real time.

The medium can be a usual animal cell medium, for example, DMEM, BME, Ham's F12, RPMI1640, a Fisher medium, an ES medium, or a primate ES medium as a basal medium, appropriately supplemented with antibiotics (e.g., penicillin and streptomycin), serum (e.g., fetal bovine serum), protein factors (e.g., basic fibroblast growth factor (bFGF), transferrin, insulin, and leukemia inhibitory factor (LIF)), nonessential amino acids, and mercaptoethanol.

The culture may be any of solid culture, liquid culture, and the like and can be performed, for example, at a temperature ranging from 35 to 40° C. in an atmosphere of air containing $CO_2$ gas, if necessary using feeder cells such as fibroblasts.

In the case of using the non-human animal of the present invention, the animal can be analyzed at the individual level. The luminescence or fluorescence signal can be measured quantitatively in a living animal individual in the presence of oxidative stress, for example, using IVIS Imaging System (Xenogen Corp.). This method is capable of histologically examining cells placed under oxidative stress. In the case of using an animal with the oxidative stress-related disease as the non-human animal, the relation of the oxidative stress to the disease can be examined visually. Meanwhile, the animal can be used for developing anti-oxidative stress drugs, i.e., therapeutic drugs for the disease. In the case of using, for example, a non-human animal having a luciferase gene in the nucleic acid construct, the luminescence signal can be obtained merely by injecting a luciferase substrate to the animal. In this case, the luminescence can be detected according to oxidative stress. The luciferase substrate is, for example, luciferin. The luciferin is converted to a luminescent substance by oxidation with luciferase.

In the case of carrying out the method for measuring oxidative stress according to the present invention using the non-human animal, the non-human animal can be subjected to tests repetitively. Specifically, the non-human animal is exposed to oxidative stress and allowed to recover from the influence of oxidative stress for a given period. When the non-human animal is exposed again to oxidative stress, the oxidative stress can be measured using this non-human animal. As a result, the measurement method of the present invention can be applied to cases in need of evaluation over time, diseases that progress over a long time, etc. The period is, for example, 1 day or longer, preferably 2 days or longer, more preferably 3 days or longer, and, for example, 10 days or shorter, preferably 7 days or shorter, more preferably 5 days or shorter, most preferably approximately 4 days.

6. Screening Method

The present invention further provides a method for screening for an anti-oxidative stress agent, comprising providing the cell or the non-human animal of the present invention with certain oxidative stress in the presence of a candidate agent and determining that the candidate agent has an anti-oxidative stress ability when the intensity of a detectable signal (e.g., a luminescence or fluorescence signal) is lower than that of a control free from the agent.

The candidate agent can be selected from natural products, non-natural products (or synthetic products), organic substances, inorganic substances, low-molecular-weight compounds, proteins, glycoproteins, lipoproteins, peptides, sugars, lipids, nucleic acids, nucleotides, oligonucleotides, polynucleotides, nucleosides, etc., or from therapeutic agents or biologically active substances known in the art, etc. Particularly, a therapeutic agent or a biologically active substance known in the art may be screened for as a newly found substance previously unknown to have an anti-oxidative stress effect. Such a substance having an anti-oxidative stress effect may further serve as a therapeutic drug for oxidative stress-related diseases such as cardiovascular diseases (e.g., atherosclerosis), neurodegenerative diseases (e.g., Alzheimer's disease, Parkinson's disease, and Huntington's disease), degenerative diseases of each organ (including liver disease), diabetes mellitus, and rheumatoid arthritis.

When the non-human animal of the present invention comprises, for example, the nucleic acid construct for oxidative stress indicator expression and a nucleic acid construct for endoplasmic reticulum stress indicator expression, this animal can be used for screening for an agent inhibiting oxidative stress and/or endoplasmic reticulum stress. The endoplasmic reticulum stress is related to neurodegenerative diseases, metabolic diseases such as diabetes mellitus, hyperlipidemia, and obesity, and other diseases such as chronic inflammation and cancer, as mentioned above. Use of this animal allows finding of an anti-stress agent for each stress. The animal that has thus acquired an additional function together with the oxidative stress indicator can be used in analysis on the state of oxidative stress as well as additional in vivo reaction, etc., through the appropriate use of its functions.

The screening method can be carried out according to the approach or the experimental system described in "5. Method for measuring oxidative stress".

Specifically, in the case of using the cell of the present invention, a candidate agent is added to a medium before, simultaneously with, or after application of stress to cultured cells. The cells are cultured, and an detectable signal, for example, an intracellular luminescence or fluorescence signal, is measured and compared with that of a control (free from the candidate agent) to select a substance capable of decreasing the signal.

In the case of using the non-human animal of the present invention, a candidate agent is administered to the animal through an administration route such as oral administration, intravenous administration, intrarectal administration, hypodermic administration, intramuscular administration, or transmucosal administration, before, simultaneously with, or after application of oxidative stress to the animal. Alternatively, the animal is fed with the candidate agent together with food. A detectable signal such as a fluorescence or luminescence signal is measured to select an agent capable of decreasing the signal.

When the non-human animal of the present invention is an animal prepared by mating with an animal with the oxidative stress-related disease, a therapeutic effect on the disease can also be determined. Thus, use of such an animal may allow easy finding of a therapeutic agent for the disease.

The agent thus screened for can be prepared into the form of a pharmaceutical agent in combination with an excipient, a solvent, or a carrier. The pharmaceutical agent can be formulated as various preparations such as solid preparations (e.g., tablets, granules, powders, and capsules), liquid preparations (e.g., solutions and suspensions), aerosol preparations, and sustained-release preparations (e.g., enteric-coated preparations, multilayer preparations, and coated preparations). For such formulation, various additives, for example, a disintegrant, a binder, a stabilizer, a lubricant, an emulsifier, a flavor, and a coloring agent can be added appropriately to the preparation.

EXAMPLES

The present invention will be described more specifically with reference to Examples below. However, the scope of the present invention is not limited to these Examples.

Example 1

<Method>

[Construction of Plasmid]

In order to prepare p(3×ARE)TKbasal, an ARE fragment (mouse GSTYa promoter-derived; ACTAGTACTAGTG-GAAATGACATTGCTAATGGT-GACAAAGCAACTTTTCTAGA (SEQ ID NO: 14) wherein added restriction sites are indicated in boldface type) amplified by PCR was digested with SpeI-XbaI and self-ligated to form a 3-repeat fragment, which was then inserted to pTKbasal having an XbaI-SpeI site. The XbaI-SpeI site is positioned at the 5' site of the TK basal promoter. Each cDNA encoding human Nrf2 (amino acids 1-93, amino acids 1-433, or full length shown in FIG. 1) was amplified by PCR. The amplification product was inserted into p(3× ARE)TKbasal (or pTKX shown in FIG. 6) having a KpnI-XhoI site. cDNA encoding luciferase (GL4) was amplified by PCR using a 1× Flag tag at its 3' end. The amplification product was inserted into p(3×ARE)TKbasal-hNrf2(1-433) having an XhoI-NheI site. The obtained p(3×ARE)TKbasal-hNrf2(1-433)-GL4-Flag was used as an OKD48-Luc plasmid. A GFP version, i.e., p(3×ARE)TKbasal-hNrf2(1-433)-Venus-Flag, was prepared by a similar approach and used as an OKD48-Venus plasmid.

A human Nrf2 overexpression vector (pCAX-hNrf2) was constructed by the insertion of a PCR-amplified human Nrf2 fragment into pCAX having KpnI-XhoI. Also, a human Keap1 overexpression vector (pCAX-hKeap1) was constructed by the insertion of a PCR-amplified human Keap1 fragment into pCAX having a HindIII-XhoI site. A terminally truncated version pCAX-hKeap1(1-314) was constructed by a similar approach.

[Cell Culture, Transfection, and Treatment]

HeLa cells or HEK293T cells were cultured in a DMEM medium supplemented with 100 U/ml penicillin, 100 µg/ml streptomycin, and 10% fetal bovine serum at 37° C. in an atmosphere containing 5% $CO_2$. The plasmid DNAs were inserted into the cells of each line using the calcium phosphate-DNA precipitation method. In order to test cellular response to agents, the cells were treated with 10 µM sodium arsenite (ASN), 100 µM diethyl maleate (DEM), 200 µM $H_2O_2$, 2.5 µg/ml tunicamycin, 1 µM thapsigargin, 1 mM DTT, 100 µM etoposide, or 100 µg/ml thenoyltrifluoroacetone (TTFA) over varying times.

[Luciferase Assay]

In dual luciferase assay using the OKD48-Luc reporter, phRL-TK (Promega Corp.) was used as an internal control. The HeLa cells were seeded on a 24-well plate and then transfected with the plasmid DNAs. At 24 hours after the transfection, the cells were lysed for luciferase assay. Each reporter activity was measured using a luciferase assay system (Promega Corp.) and a luminometer (Berthold Japan Co., Ltd.). The results were shown as mean±SEM of three experiments. Each value was indicated in terms of fold induction. This fold induction was normalized for that of an untreated sample (NT) (FIG. 5A), an untreated sample (NT) free from Nrf2 overexpression (FIG. 5D), or an untreated sample (NT) free from Keap1 overexpression (FIG. 5E). In this calculation, the fold induction of each NT was defined as 1.0.

[Fluorescence Imaging and Fluorescence Intensity Measurement]

In order to take images of the cells, the HEK293T cells were seeded over a 6-well plate and then transfected with the plasmid DNAs. At 24 hours after the transfection, fluorescence images were obtained using FSX100 (Olympus Corp.). In order to measure the fluorescence of cell lysates, the cells were lysed in a digitonin buffer (50 mM Tris-HCl (pH 7.5), 1 mM EDTA, 10 mM EGTA, and 10 µM digitonin) at 37° C. for 30 minutes. The lysates were rendered transparent by centrifugation at 16,500 g. The fluorescence of the supernatant was measured (emission wavelength: 535 nm; excitation wavelength: 485 nm) using a fluorometer (ARVO MX-2, PerkinElmer, Inc.). pCAG-GL3 was used as an internal control. The fluorescence intensity of each sample was normalized against the activity of luciferase derived from the cotransfected cells. Each value was shown as mean±SEM of three experiments.

[Western Blot Analysis]

The cells were lysed in an SDS sample buffer (50 mM Tris-HCl (pH 6.8), 2% SDS, 50 mM DTT, 10% glycerol, and 1 µg/ml bromophenol blue). The lysates were heated at 98° C. for 10 minutes. Proteins in the lysates were separated using SDS-PAGE. After the electrophoresis, the proteins were electrically transferred to a polyvinylidene fluoride porous membrane and immunologically detected by a standard approach using a monoclonal antibody against luciferase (Promega Corp.), a monoclonal antibody against GFP (Nacalai Tesque, Inc.), a monoclonal antibody against GAPDH (Cell Signaling Technology, Inc.), or a polyclonal antibody against Nrf2 (Santa Cruz Biotechnology, Inc.).

[Transgenic Mouse]

The 4.5-kb SpeI-SfiI fragment of p(3×ARE)TKbasal-hNrf2(1-433)-GL4-Flag was microinjected as a transgene into the fertilized eggs of a C57BL/6 mouse. Transgenic offspring was screened for by PCR using primers represented by 5'-ATC ACC AGA ACA CTC AGT GG-3' (SEQ ID NO: 15) and 5'-ACT CGG CGT AGG TAA TGT CC-3' (SEQ ID NO: 16). The obtained mouse was used for in vivo imaging assay. After intraperitoneal injection of D-luciferin (4.5 mg), the mouse was analyzed according to a standard protocol using an in vivo imaging system IVIS (Xenogen Corp.). The experimental protocol involving the animal was approved by the animal research committee of RIKEN (Japan).

<Results>

[Design and Construction of Novel Oxidative Stress Indicator (OKD48)]

This time, the present inventors used the Keap1-Nrf2 pathway in the preparation of OKD48, a novel type of oxidative stress indicator. A partial fragment of Nrf2 related to stress-dependent stabilization was fused with a luciferase (Luc) gene and expressed under the control of a stress-inducible promoter. As shown in FIG. 3, endogenous Nrf2 is absent in the nucleus in a normal state. Thus, neither is reporter expression induced at the transcriptional level, nor leaked reporter proteins produce a detectable signal because Keap1-mediated degradation is inhibited. Under oxidative stress, however, the transcription of the reporter gene is induced along with the increased amount of endogenous Nrf2 and its nuclear translocation. In addition, the inhibition of Keap1-mediated degradation is also canceled. Thus, reporter protein expression is enhanced to produce a detectable signal.

Figure 6A:
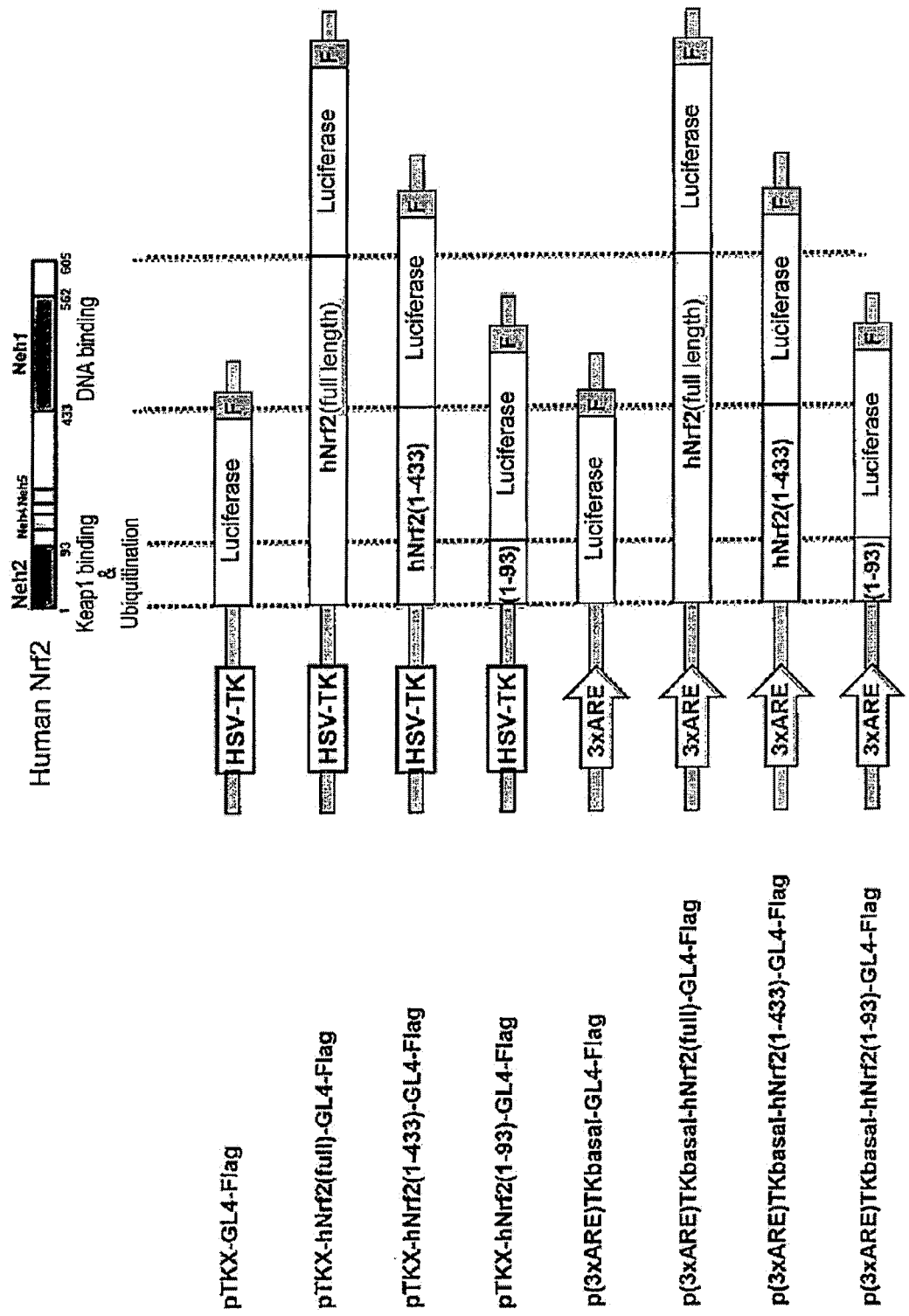
FIG. 6A is a schematic diagram of a test construct. The partial fragment (amino acids 1-93 or amino acids 1-433) or full length coding sequence of human Nrf2 was fused with a Flag-tagged luciferase (GL4) coding sequence. These fusion genes were driven by a 3×ARE promoter or a herpes simplex virus thymidine kinase (HSV-TK) promoter as a negative control.
Figure 6B:
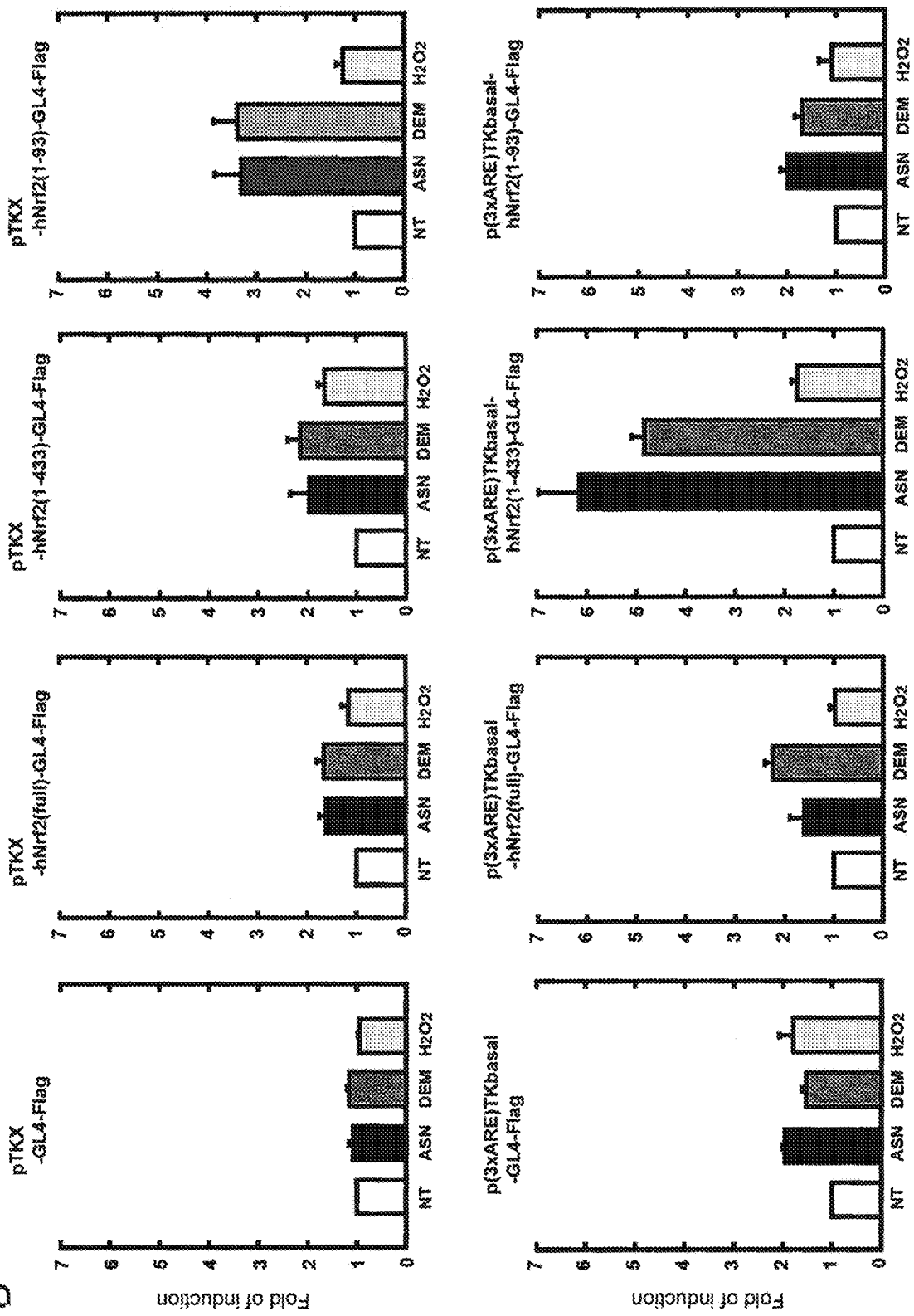
FIG. 6B shows luciferase assay using a test construct. HeLa cells were transfected with each test construct and treated for 8 hours or 16 hours in the presence or absence of sodium arsenite (ASN), diethyl maleate, or $H_2O_2$, followed by luciferase assay.

As exemplarily shown in FIG. 6, some variations of partial fragments of Nrf2 and promoters used in combination were prepared and searched for a combination exhibiting the highest response. Amino acids (a.a.) 1-93, 1-433, and full length were examined as the Nrf2 fragments. An HSV-TK promoter used as a negative control as well as an HO-1 enhancer and a 3×ARE promoter were studied as the promoters. As a result, the combination of the Nrf2 a.a. 1-433 region and the 3×ARE promoter exhibited the highest response to an oxidative stress-inducing agent ASN or DEM.

[In Vitro OKD48 Characterization]

Figure 5:
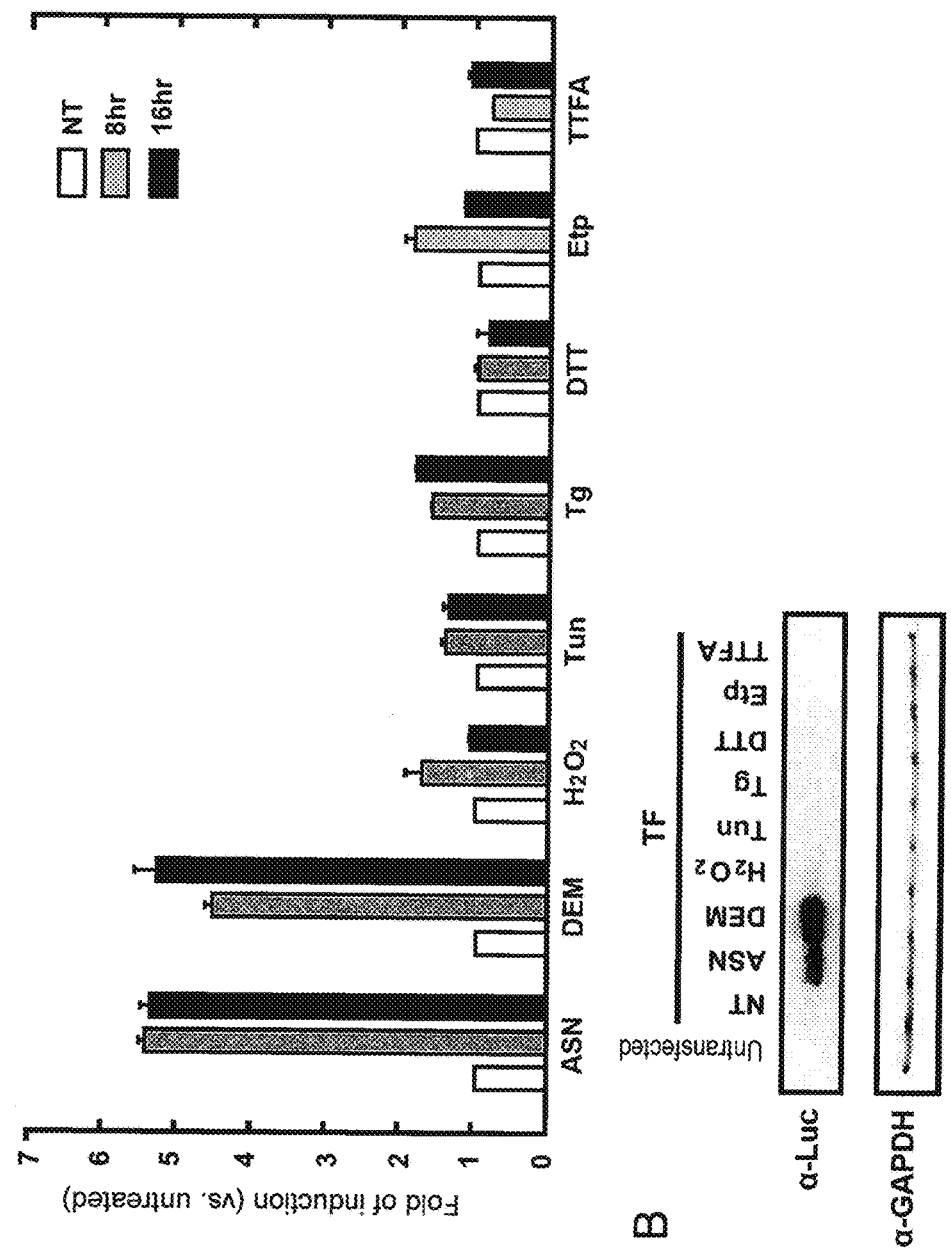
FIG. 5 shows the in vitro characterization of OKD48.
Figure 5:
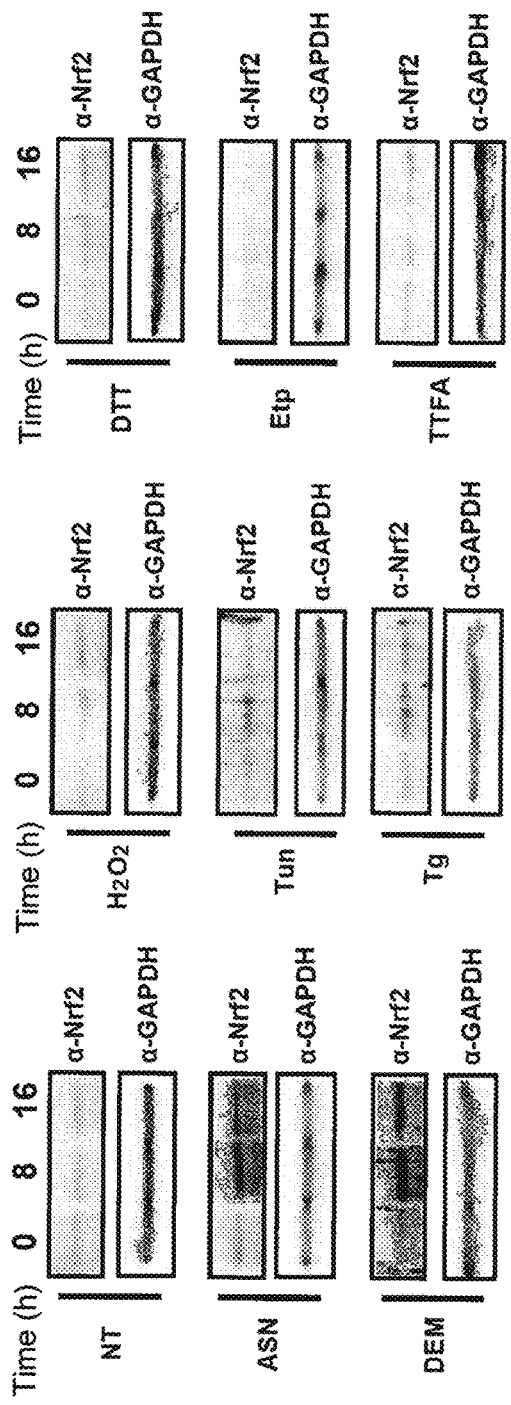
Figure 5:
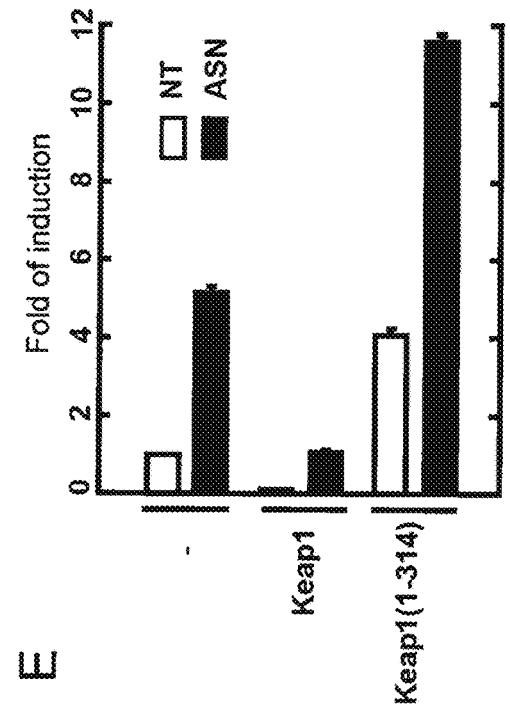
Figure 5:
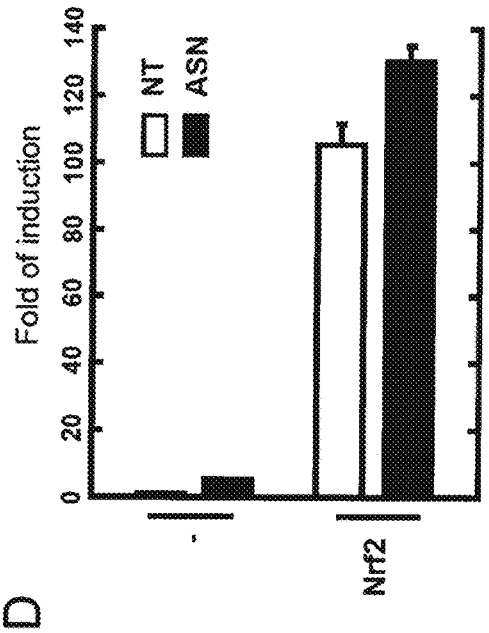

In order to test the OKD48 (ARE-Nrf2 jointed stress associated indicator)-Luc thus constructed for the presence or absence of its function as an oxidative stress indicator in actual mammal cells, an expression vector of the fusion gene was introduced into cultured cells, followed by assay (FIG. 5). HeLa cells were evaluated for their response to different agents by luciferase assay. As a result, the cells containing OKD48-Luc specifically responded to oxidative stress-inducing agents such as sodium arsenite (ASN) or diethyl maleate (DEM) and were rarely activated by endoplasmic reticulum stress-inducing agents such as tunicamycin (Tun) or thapsigargin (Tg), a reducing agent dithiothreitol (DTT), an apoptosis-inducing topoisomerase II inhibitor etoposide (Etp), or a chemical hypoxia-inducing agent thenoyltrifluoroacetone (TTFA) (FIG. 5A). The results of Western blot using an anti-Luc antibody, which are consistent with the results of this reporter assay, demonstrated an ASN- or DEM-specific rise in OKD48-Luc at the protein level (FIG. 5B). As shown in FIG. 5C, among these agents, only ASN and DEM significantly induced endogenous Nrf2. These results show that the specificity of the prepared reporter is identical to that of endogenous Nrf2 and mean that OKD48-Luc is useful as an oxidative stress indicator.

Next, the present inventors examined the influence of overexpression of related factors on OKD48-Luc. As shown in FIG. 5D, Nrf2 overexpression increased the activity of OKD48-Luc by 100 times or more even under normal conditions. This activity was further slightly increased by ASN treatment. By contrast, Keap1 overexpression reduced the activity of OKD48-Luc regardless of the presence or absence of stress, whereas the overexpression of Keap1(1-314), which was deficient in an Nrf2 binding region, increased the activity of OKD48-Luc (FIG. 5E). These results support the model prepared on the assumption that OKD48-Luc would be induced by Nrf2 and undergo the control of degradation and stabilization by Keap1.

Figure 7:
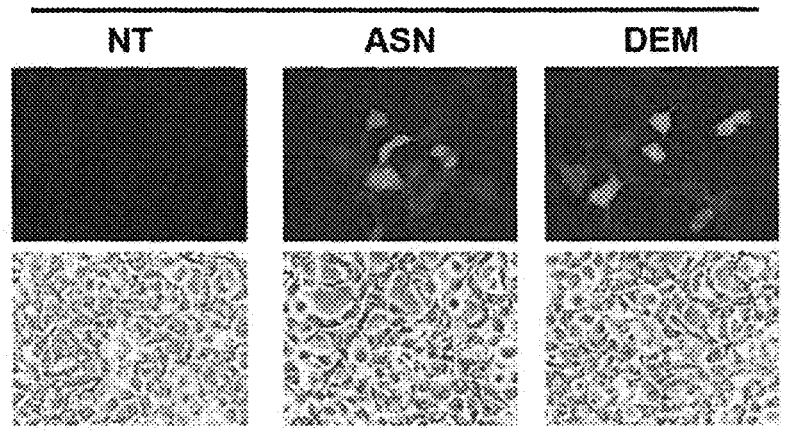
FIG. 7 shows the in vitro detection of fluorescence from OKD48-Venus.
Figure 7:
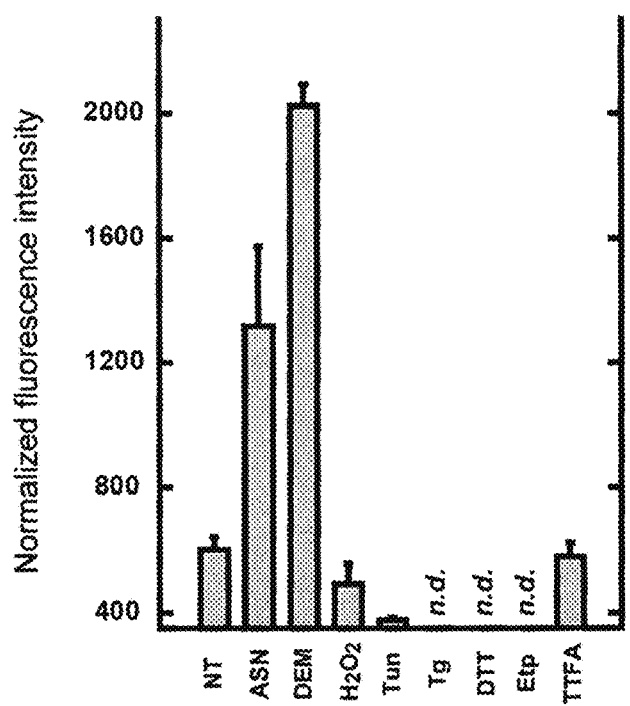
Figure 7:
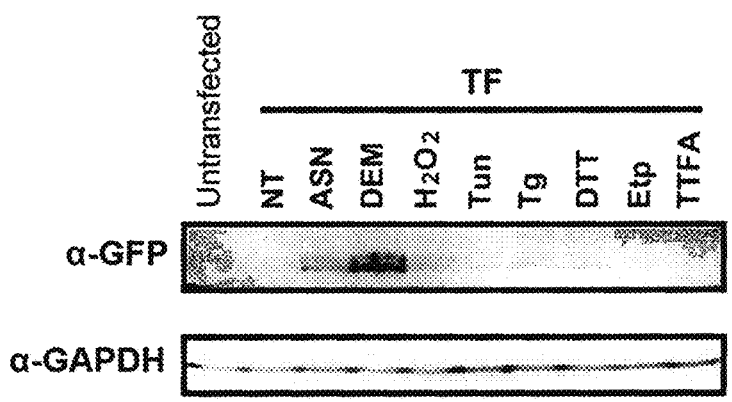

In addition to such a luciferase-fused reporter, a GFP-fused reporter (OKD48-Venus) was also prepared and checked in cultured cells (FIG. 7). OKD48-Venus, as in the Luc-fused reporter, emitted fluorescence along with ASN or DEM treatment under microscopic observation (FIG. 7A). Similar results were also confirmed in fluorescence assay using cell lysates (FIG. 7B) and Western blot using an anti-GFP antibody (FIG. 7C).

[Preparation of OKD48 Mouse and In Vivo Monitoring of Oxidative Stress]

Figure 8:
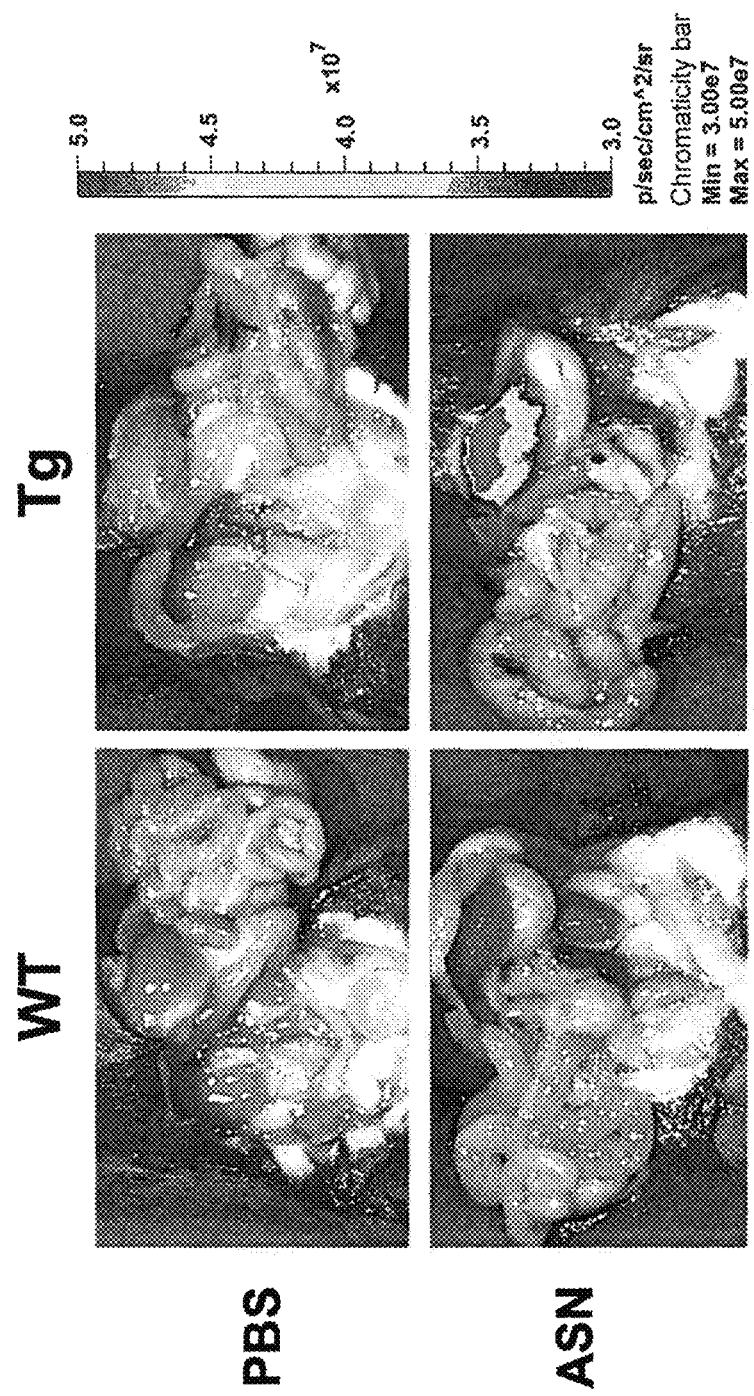
FIG. 8 shows the observation of a luminescence signal in a mouse that underwent abdominal surgery 6 hours after administration of an ASN reagent as an oxidative stressor.

In order to monitor oxidative stress in vivo, an OKD48-transgenic mouse having a 3×ARE-driven Nrf2(1-433)-Luc expression gene was prepared. In order to confirm that cells placed under oxidative stress were able to be effectively used in vivo, ASN inducing oxidative stress in various tissues or organs was intraperitoneally injected (12.5 mg/kg) to a transgenic mouse. Six hours later, a luminescence signal was observed under abdominal section. The ASN-injected transgenic mouse exhibited strong luminescence in the liver (FIG. 8). Luminescence was also detected to some extent in other tissues or organs (e.g., stomach and kidney; data not shown). In contrast to this, a PBS-injected control transgenic mouse rarely exhibited luminescence. These results show that the prepared transgenic mouse can be used in the detection of oxidative stress in animal individuals.

Example 2

[Preparation of Mouse OKD48 and its Property]

Figure 9:
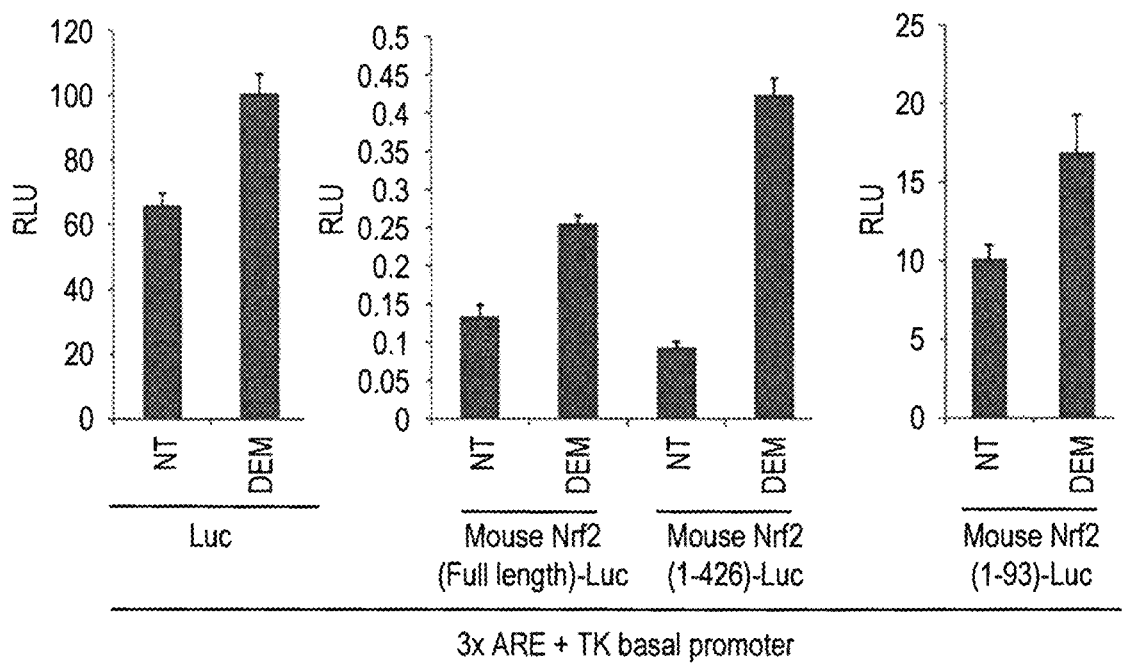
FIG. 9 shows the luminescence properties of mouse OKD48 under stress conditions (stressor: DEM or ASN).
Figure 9:
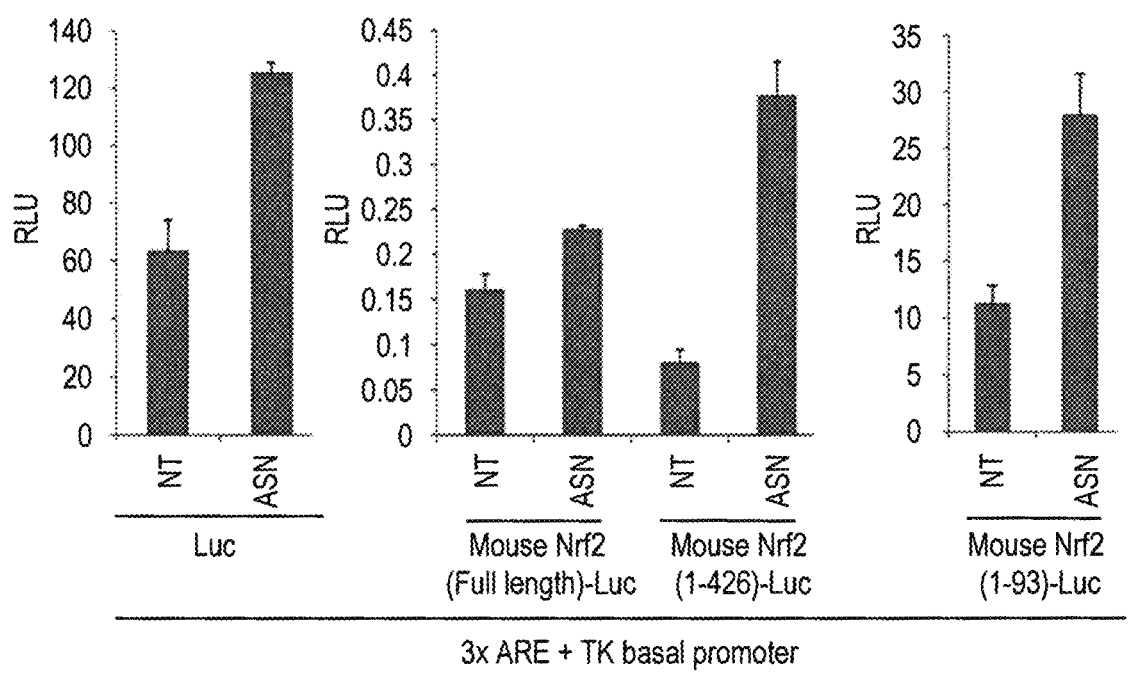

Mouse OKD48-Luc (3×ARE+TK basal promoter+mouse Nrf2(1-426)+Luc) was prepared in an approach similar to Example 1 and introduced into HeLa cells, which were then treated with an oxidative stressor (DEM or ASN). Luminescence intensity was measured by luciferase assay. As a result, mouse Nrf2(1-426)-Luc exhibited the highest S/N ratio compared with mouse Nrf2(1-93) and mouse Nrf2 (full), both in the case of DEM and in the case of ASN (FIG. 9).

INDUSTRIAL APPLICABILITY

The indicator of the present invention enables cells or tissues placed under oxidative stress to be visually grasped in vivo, in order to specifically detect oxidative stress related to the Nrf2-Keap1 pathway in cells or animals. The indicator of the present invention also contributes to pathological research on various oxidative stress-related diseases and the development of therapeutic agents therefor using a non-human animal capable of expressing the indicator.

FREE TEXT OF SEQUENCE LISTING

SEQ ID NO: 3: HSV-TK basal promoter
SEQ ID NO: 7: Mouse HO-1 enhancer-TK basal promoter
SEQ ID NO: 10:3×ARE
SEQ ID NO: 11: 3×ARE-TK basal promoter
SEQ ID NO: 12: 3×ARE-TKbasal-OKD48-Luc
SEQ ID NO: 13: 3×ARE-TKbasal-OKD48-Venus
SEQ ID NO: 15: Primer
SEQ ID NO: 16: Primer All publications, patents, and patent applications cited herein are incorporated herein by reference in their entirety.

The invention claimed is:

1. A nucleic acid construct for expressing an indicator that detects Nrf2-KEAP1-associated oxidative stress comprising:
   a first Nrf2 nucleic acid sequence encoding a Neh2-Neh6 domain sequence of a human or mouse Nrf2 protein, wherein the Neh2-Neh6 domain sequence consists of amino acids 1-433 (human) or amino acids 1-425 (mouse) in the amino acid sequence of the Nrf2 protein represented by SEQ ID NO: 1 (human) or SEQ ID NO: 2 (mouse), respectively;
   a first stress-inducible promoter sequence positioned upstream of the first Nrf2 nucleic acid sequence, wherein the first stress-inducible promoter sequence comprises a combination of three copies of antioxidant responsive element (ARE) and a promoter, wherein the ARE comprises the sequence of TGA(G/C)NNNGC where N represents G, C, A, or T; and
   a first reporter nucleic acid sequence encoding a protein capable of generating a detectable signal, the first reporter nucleic acid sequence being positioned downstream of the nucleic acid sequence encoding the Neh2-Neh6 domain sequence;
   wherein the nucleic acid construct does not encode Neh1-Neh3 domain of the Nrf2 protein;
   wherein the first Nrf2 nucleic acid sequence and the first reporter nucleic acid sequence are under control of the first stress-inducible promoter sequence in expression of the first Nrf2 nucleic acid and the first reporter nucleic acid; and
   wherein the nucleic acid construct exhibits increased sensitivity in detecting Nrf2-KEAP1-associated oxidative stress compared to that observed in a second nucleic acid construct comprising
   a second Nrf2 nucleic acid sequence encoding a second Nrf2 protein wherein the second Nrf2 protein sequence consists of amino acids 1-93 in the amino acid sequence of the Nrf2 protein represented by SEQ ID NO: 1 (human) or SEQ ID NO: 2 (mouse) respectively;
   a second stress-inducible promoter sequence positioned upstream of the second Nrf2 nucleic acid sequence, wherein the second stress-inducible promoter sequence is identical to the first stress-inducible promoter sequence; and
   a second reporter nucleic acid positioned downstream of the second Nrf2 nucleic acid sequence, wherein the second reporter nucleic acid sequence is identical to the first reporter nucleic acid sequence; and
   wherein the second Nrf2 nucleic acid sequence and the second reporter nucleic acid sequence are under control of the second stress-inducible promoter sequence in expression of the second Nrf2 nucleic acid and the second reporter nucleic acid.

2. The nucleic acid construct according to claim 1, wherein the nucleic acid construct comprises a tag coding sequence at its 3' end.

3. The nucleic acid construct according to claim 2, wherein the tag coding sequence is a Flag tag coding sequence.

4. The nucleic acid construct according to claim 1, wherein the promoter is selected from the group consisting of HSV-TK basal promoters, HSV-TK promoters, cytomegalovirus (CMV) promoters, and SV-40 virus promoters.

5. The nucleic acid construct according to claim 1, wherein the ARE comprises the nucleotide sequence of SEQ ID NO: 8 and/or the nucleotide sequence of SEQ ID NO: 9.

6. A vector comprising a nucleic acid construct according to claim 1.

7. A cell comprising a nucleic acid construct according to claim 1.

8. A non-human animal comprising a nucleic acid construct according to claim 1.

9. The non-human animal according to claim 8, wherein the non-human animal further comprises a nucleic acid construct for endoplasmic reticulum stress indicator expression or a nucleic acid construct for hypoxic stress indicator expression.

10. A method for measuring oxidative stress, comprising measuring the intensity of a detectable signal increased in a cell according to claim 7.

11. A method for screening for an anti-oxidative stress agent, comprising providing a cell according to claim 7 with oxidative stress in the presence of a candidate agent and determining that the candidate agent has an anti-oxidative stress ability when the intensity of a detectable signal is lower than that of a control measured in the absence of the candidate agent.

12. A method for measuring oxidative stress, comprising measuring the intensity of a detectable signal increased in a non-human animal according to claim 8 that is provided with oxidative stress.

13. A method for screening for an anti-oxidative stress agent, comprising providing a non-human animal according to claim 8 with oxidative stress in the presence of a candidate agent and determining that the candidate agent has an anti-oxidative stress ability when the intensity of a detectable signal is lower than that of a control measured in the absence of the candidate agent.

* * * * *

SEQUENCE LISTING

```
<160> NUMBER OF SEQ ID NOS: 16

<210> SEQ ID NO 1
<211> LENGTH: 604
<212> TYPE: PRT
<213> ORGANISM: Homo sapiens

<400> SEQUENCE: 1

Met Asp Leu Glu Leu Pro Pro Pro Gly Leu Pro Ser Gln Gln Asp Met
1               5                   10                  15

Asp Leu Ile Asp Ile Leu Trp Arg Gln Asp Ile Asp Leu Gly Val Ser
            20                  25                  30
```

```
Arg Glu Val Phe Asp Phe Ser Gln Arg Arg Lys Glu Tyr Glu Leu Glu
            35                  40                  45
Lys Gln Lys Lys Leu Glu Lys Glu Arg Gln Glu Gln Leu Gln Lys Glu
 50                  55                  60
Gln Glu Lys Ala Phe Phe Ala Gln Leu Gln Leu Asp Glu Glu Thr Gly
 65                  70                  75                  80
Glu Phe Leu Pro Ile Gln Pro Ala Gln His Ile Gln Ser Glu Thr Ser
                 85                  90                  95
Gly Ser Ala Asn Tyr Ser Gln Val Ala His Ile Pro Lys Ser Asp Ala
                100                 105                 110
Leu Tyr Phe Asp Asp Cys Met Gln Leu Leu Ala Gln Thr Phe Pro Phe
            115                 120                 125
Val Asp Asp Asn Glu Val Ser Ser Ala Thr Phe Gln Ser Leu Val Pro
130                 135                 140
Asp Ile Pro Gly His Ile Glu Ser Pro Val Phe Ile Ala Thr Asn Gln
145                 150                 155                 160
Ala Gln Ser Pro Glu Thr Ser Val Ala Gln Val Ala Pro Val Asp Leu
                165                 170                 175
Asp Gly Met Gln Gln Asp Ile Glu Gln Val Trp Glu Glu Leu Leu Ser
            180                 185                 190
Ile Pro Glu Leu Gln Cys Leu Asn Ile Glu Asn Asp Lys Leu Val Glu
            195                 200                 205
Thr Thr Met Val Pro Ser Pro Glu Ala Lys Leu Thr Glu Val Asp Asn
            210                 215                 220
Tyr His Phe Tyr Ser Ser Ile Pro Ser Met Glu Lys Glu Val Gly Asn
225                 230                 235                 240
Cys Ser Pro His Phe Leu Asn Ala Phe Glu Asp Ser Phe Ser Ser Ile
                245                 250                 255
Leu Ser Thr Glu Asp Pro Asn Gln Leu Thr Val Asn Ser Leu Asn Ser
            260                 265                 270
Asp Ala Thr Val Asn Thr Asp Phe Gly Asp Glu Phe Tyr Ser Ala Phe
            275                 280                 285
Ile Ala Glu Pro Ser Ile Ser Asn Ser Met Pro Ser Pro Ala Thr Leu
            290                 295                 300
Ser His Ser Leu Ser Glu Leu Leu Asn Gly Pro Ile Asp Val Ser Asp
305                 310                 315                 320
Leu Ser Leu Cys Lys Ala Phe Asn Gln Asn His Pro Glu Ser Thr Ala
                325                 330                 335
Glu Phe Asn Asp Ser Asp Ser Gly Ile Ser Leu Asn Thr Ser Pro Ser
            340                 345                 350
Val Ala Ser Pro Glu His Ser Val Glu Ser Ser Ser Tyr Gly Asp Thr
            355                 360                 365
Leu Leu Gly Leu Ser Asp Ser Glu Val Glu Glu Leu Asp Ser Ala Pro
            370                 375                 380
Gly Ser Val Lys Gln Asn Gly Pro Lys Thr Pro Val His Ser Ser Gly
385                 390                 395                 400
Asp Met Val Gln Pro Leu Ser Pro Ser Gln Gln Ser Thr His Val
                405                 410                 415
His Asp Ala Gln Cys Glu Asn Thr Pro Glu Lys Glu Leu Pro Val Ser
            420                 425                 430
Pro Gly His Arg Lys Thr Pro Phe Thr Lys Asp Lys His Ser Ser Arg
            435                 440                 445
```

-continued

```
Leu Glu Ala His Leu Thr Arg Asp Glu Leu Arg Ala Lys Ala Leu His
450                 455                 460

Ile Pro Phe Pro Val Glu Lys Ile Ile Asn Leu Pro Val Val Asp Phe
465                 470                 475                 480

Asn Glu Met Met Ser Lys Glu Gln Phe Asn Glu Ala Gln Leu Ala Leu
                485                 490                 495

Ile Arg Asp Ile Arg Arg Gly Lys Asn Lys Val Ala Ala Gln Asn
            500                 505                 510

Cys Arg Lys Arg Lys Leu Glu Asn Ile Val Glu Leu Glu Gln Asp Leu
            515                 520                 525

Asp His Leu Lys Asp Glu Lys Glu Lys Leu Leu Lys Glu Lys Gly Glu
530                 535                 540

Asn Asp Lys Ser Leu His Leu Leu Lys Lys Gln Leu Ser Thr Leu Tyr
545                 550                 555                 560

Leu Glu Val Phe Ser Met Leu Arg Asp Glu Asp Gly Lys Pro Tyr Ser
                565                 570                 575

Pro Ser Glu Tyr Ser Leu Gln Gln Thr Arg Asp Gly Asn Val Phe Leu
                580                 585                 590

Val Pro Lys Ser Lys Lys Pro Asp Val Lys Lys Asn
            595                 600
```

<210> SEQ ID NO 2
<211> LENGTH: 596
<212> TYPE: PRT
<213> ORGANISM: Mus musculus

<400> SEQUENCE: 2

```
Met Asp Leu Glu Leu Pro Pro Gly Leu Gln Ser Gln Gln Asp Met
1               5                   10                  15

Asp Leu Ile Asp Ile Leu Trp Arg Gln Asp Ile Asp Leu Gly Val Ser
                20                  25                  30

Arg Glu Val Phe Asp Phe Ser Gln Arg Gln Lys Asp Tyr Glu Leu Glu
            35                  40                  45

Lys Gln Lys Lys Leu Glu Lys Glu Arg Gln Glu Gln Leu Gln Lys Glu
50                  55                  60

Gln Glu Lys Ala Phe Phe Ala Gln Phe Gln Leu Asp Glu Glu Thr Gly
65                  70                  75                  80

Glu Phe Leu Pro Ile Gln Pro Ala Gln His Ile Gln Thr Asp Thr Ser
                85                  90                  95

Gly Ser Ala Ser Tyr Ser Gln Val Ala His Ile Pro Lys Gln Asp Ala
            100                 105                 110

Leu Tyr Phe Glu Asp Cys Met Gln Leu Leu Ala Glu Thr Phe Pro Phe
        115                 120                 125

Val Asp Asp His Glu Ser Leu Ala Asp Ile Pro Ser His Ala Glu
    130                 135                 140

Ser Ser Val Phe Thr Ala Pro His Gln Ala Gln Ser Leu Asn Ser Ser
145                 150                 155                 160

Leu Glu Ala Ala Met Thr Asp Leu Ser Ser Ile Glu Gln Asp Met Glu
                165                 170                 175

Gln Val Trp Gln Glu Leu Phe Ser Ile Pro Glu Leu Gln Cys Leu Asn
            180                 185                 190

Thr Glu Asn Lys Gln Leu Ala Asp Thr Thr Ala Val Pro Ser Pro Glu
        195                 200                 205

Ala Thr Leu Thr Glu Met Asp Ser Asn Tyr His Phe Tyr Ser Ser Ile
    210                 215                 220
```

-continued

Ser Ser Leu Glu Lys Glu Val Gly Asn Cys Gly Pro His Phe Leu His
225                 230                 235                 240

Gly Phe Glu Asp Ser Phe Ser Ser Ile Leu Ser Thr Asp Asp Ala Ser
            245                 250                 255

Gln Leu Thr Ser Leu Asp Ser Asn Pro Thr Leu Asn Thr Asp Phe Gly
            260                 265                 270

Asp Glu Phe Tyr Ser Ala Phe Ile Ala Glu Pro Ser Asp Gly Gly Ser
            275                 280                 285

Met Pro Ser Ser Ala Ala Ile Ser Gln Ser Leu Ser Glu Leu Leu Asp
290                 295                 300

Gly Thr Ile Glu Gly Cys Asp Leu Ser Leu Cys Lys Ala Phe Asn Pro
305                 310                 315                 320

Lys His Ala Glu Gly Thr Met Glu Phe Asn Asp Ser Asp Ser Gly Ile
            325                 330                 335

Ser Leu Asn Thr Ser Pro Ser Arg Ala Ser Pro Glu His Ser Val Glu
            340                 345                 350

Ser Ser Ile Tyr Gly Asp Pro Pro Gly Phe Ser Asp Ser Glu Met
            355                 360                 365

Glu Glu Leu Asp Ser Ala Pro Gly Ser Val Lys Gln Asn Gly Pro Lys
370                 375                 380

Ala Gln Pro Ala His Ser Pro Gly Asp Thr Val Gln Pro Leu Ser Pro
385                 390                 395                 400

Ala Gln Gly His Ser Ala Pro Met Arg Glu Ser Gln Cys Glu Asn Thr
            405                 410                 415

Thr Lys Lys Glu Val Pro Val Ser Pro Gly His Gln Lys Ala Pro Phe
            420                 425                 430

Thr Lys Asp Lys His Ser Ser Arg Leu Glu Ala His Leu Thr Arg Asp
            435                 440                 445

Glu Leu Arg Ala Lys Ala Leu His Ile Pro Phe Pro Val Glu Lys Ile
450                 455                 460

Ile Asn Leu Pro Val Asp Asp Phe Asn Glu Met Met Ser Lys Glu Gln
465                 470                 475                 480

Phe Asn Glu Ala Gln Leu Ala Leu Ile Arg Asp Ile Arg Arg Arg Gly
            485                 490                 495

Lys Asn Lys Val Ala Ala Gln Asn Cys Arg Lys Arg Lys Leu Glu Asn
            500                 505                 510

Ile Val Glu Leu Glu Gln Asp Leu Gly His Leu Lys Asp Glu Arg Glu
            515                 520                 525

Lys Leu Leu Arg Glu Lys Gly Glu Asn Asp Arg Asn Leu His Leu Leu
530                 535                 540

Lys Arg Arg Leu Ser Thr Leu Tyr Leu Glu Val Phe Ser Met Leu Arg
545                 550                 555                 560

Asp Glu Asp Gly Lys Pro Tyr Ser Pro Ser Glu Tyr Ser Leu Gln Gln
            565                 570                 575

Thr Arg Asp Gly Asn Val Phe Leu Val Pro Lys Ser Lys Lys Pro Asp
            580                 585                 590

Thr Lys Lys Asn
        595

<210> SEQ ID NO 3
<211> LENGTH: 152
<212> TYPE: DNA
<213> ORGANISM: Artificial
<220> FEATURE:
<223> OTHER INFORMATION: HSV-TK basal promoter

```
<400> SEQUENCE: 3
ggccccgccc agcgtcttgt cattggcgaa ttcgaacacg cagatgcagt cggggcggcg      60
cggtccgagg tccacttcgc atattaaggt gacgcgtgtg gcctcgaaca ccgagcgacc     120
ctgcagcgac ccgcttaaca gcgtcaacag cg                                   152

<210> SEQ ID NO 4
<211> LENGTH: 216
<212> TYPE: DNA
<213> ORGANISM: herpes simplex virus

<400> SEQUENCE: 4
ccgtggcccg ttgctcgcgt ttgctggcgg tgtccccgga agaaatatat ttgcatgtct      60
ttagttctat gatgacacaa accccgccca gcgtcttgtc attggcgaat tcgaacacgc     120
agatgcagtc ggggcggcgc ggtcccaggt ccacttcgca tattaaggtg acgcgtgtgg     180
cctcgaacac cgagcgaccc tgcagcgacc cgctta                               216

<210> SEQ ID NO 5
<211> LENGTH: 203
<212> TYPE: DNA
<213> ORGANISM: simian virus 40

<400> SEQUENCE: 5
tgcatctcaa ttagtcagca accatagtcc cgcccctaac tccgcccatc ccgcccctaa      60
ctccgcccag ttccgcccat tctccgcccc atcgctgact aattttttttt atttatgcag    120 aggccgaggc cgcctcggcc tctgagctat tccagaagta gtgaggaggc ttttttggag     180
gcctaggctt ttgcaaaaag ctt                                             203

<210> SEQ ID NO 6
<211> LENGTH: 795
<212> TYPE: DNA
<213> ORGANISM: cytomegalovirus

<400> SEQUENCE: 6
tcaatattgg ccattagcca tattattcat tggttatata gcataaatca atattggcta      60
ttggccattg catacgttgt atctatatca taatatgtac attttatttg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgcccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg ccccctattg acgtcaatga     420
cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca gtctccaccc cattgacgt     600 caatgggagt ttgttttggc accaaaatca acgggacttt ccaaaatgtc gtaataaccc     660
cgccccgttg acgcaaatgg gcggtaggcg tgtacggtgg gaggtctata taagcagagc     720
tcgtttagtg aaccgtcaga tcactagaag ctttattgcg gtagtttatc acagttaaat     780
tgctaacgca gtcag                                                     795
```

<210> SEQ ID NO 7
<211> LENGTH: 432
<212> TYPE: DNA
<213> ORGANISM: Artificial
<220> FEATURE:
<223> OTHER INFORMATION: mouse HO-1 enhancer-TK basal promoter

<400> SEQUENCE: 7

```
actagtgagc tccaccccca cccaggattc cagcccccac aggagctgaa ctttgttttt     60
cccgcagcgg ctggaatgct gagttgtgat ttcctcactg ctcatttcct cagctgcttt    120
tatgctgtgt catggttggg aggggtgatt agcagacaaa gggaagacag attttgctga    180
gtcaccctct gttccctctg cctcagctag gaatagttgg taaaaggttc cggaacggct    240
ttaacttcag gcagaaggaa gtgaaagttc tagaggcccc gcccagcgtc ttgtcattgg    300
cgaattcgaa cacgcagatg cagtcggggc ggcgcggtcc gaggtccact tcgcatatta    360
aggtgacgcg tgtggcctcg aacaccgagc gaccctgcag cgacccgctt aacagcgtca    420
acagcgaagc tt                                                        432
```

<210> SEQ ID NO 8
<211> LENGTH: 9
<212> TYPE: DNA
<213> ORGANISM: Mus musculus

<400> SEQUENCE: 8

```
tgacattgc                                                              9
```

<210> SEQ ID NO 9
<211> LENGTH: 9
<212> TYPE: DNA
<213> ORGANISM: Mus musculus

<400> SEQUENCE: 9

```
tgacaaagc                                                              9
```

<210> SEQ ID NO 10
<211> LENGTH: 129
<212> TYPE: DNA
<213> ORGANISM: Artificial
<220> FEATURE:
<223> OTHER INFORMATION: 3xARE

<400> SEQUENCE: 10

```
actagtggaa atgacattgc taatggtgac aaagcaactt ttctagtgga atgacattg      60
ctaatggtga caaagcaact tttctagtgg aaatgacatt gctaatggtg acaaagcaac    120
ttttctaga                                                            129
```

<210> SEQ ID NO 11
<211> LENGTH: 287
<212> TYPE: DNA
<213> ORGANISM: Artificial
<220> FEATURE:
<223> OTHER INFORMATION: 3xARE-TK basal promoter

<400> SEQUENCE: 11

```
actagtggaa atgacattgc taatggtgac aaagcaactt ttctagtgga atgacattg      60
ctaatggtga caaagcaact tttctagtgg aaatgacatt gctaatggtg acaaagcaac    120
ttttctagag gccccgccca gcgtcttgtc attggcgaat tcgaacacgc agatgcagtc    180
```

```
ggggcggcgc ggtccgaggt ccacttcgca tattaaggtg acgcgtgtgg cctcgaacac    240
cgagcgaccc tgcagcgacc cgcttaacag cgtcaacagc gaagctt                  287
```

<210> SEQ ID NO 12
<211> LENGTH: 3283
<212> TYPE: DNA
<213> ORGANISM: Artificial
<220> FEATURE:
<223> OTHER INFORMATION: 3xARE-TKbasal-OKD48-Luc

<400> SEQUENCE: 12

```
actagtggaa atgacattgc taatggtgac aaagcaactt ttctagtgga atgacattg      60 ctaatggtga caaagcaact tttctagtgg aaatgacatt gctaatggtg acaaagcaac   120
ttttctagag gccccgccca gcgtcttgtc attggcgaat tcgaacacgc agatgcagtc   180
ggggcggcgc ggtccgaggt ccacttcgca tattaaggtg acgcgtgtgg cctcgaacac   240
cgagcgaccc tgcagcgacc cgcttaacag cgtcaacagc gaagcttcta ggtaccatga   300
tggacttgga gctgccgccg ccgggactcc cgtcccagca ggacatggat ttgattgaca   360
tactttggag gcaagatata gatcttggag taagtcgaga agtatttgac ttcagtcagc   420
gacggaaaga gtatgagctg aaaaacagaa aaaacttga aaaggaaaga caagaacaac   480
tccaaaagga gcaagagaaa gccttttcg ctcagttaca actagatgaa gagacaggtg   540
aatttctccc aattcagcca gcccagcaca tccagtcaga aaccagtgga tctgccaact   600
actcccaggt tgcccacatt cccaaatcag atgctttgta ctttgatgac tgcatgcagc   660
ttttggcgca gacattcccg tttgtagatg acaatgaggt ttcttcggct acgtttcagt   720
cacttgttcc tgatattccc ggtcacatcg agagcccagt cttcattgct actaatcagg   780
ctcagtcacc tgaaacttct gttgctcagg tagcccctgt tgatttagac ggtatgcaac   840
aggacattga gcaagtttgg gaggagctat tatccattcc tgagttacag tgtcttaata   900
ttgaaaatga caagctggtt gagactacca tggttccaag tccagaagcc aaactgacag   960
aagttgacaa ttatcatttt tactcatcta taccctcaat ggaaaaagaa gtaggtaact  1020
gtagtccaca ttttcttaat gcttttgagg attccttcag cagcatcctc tccacagaag  1080
accccaacca gttgacagtg aactcattaa attcagatgc cacagtcaac acagattttg  1140
gtgatgaatt ttattctgct ttcatagctg agcccagtat cagcaacagc atgccctcac  1200
ctgctacttt aagccattca ctctctgaac ttctaaatgg gcccattgat gtttctgatc  1260
tatcactttg caaagctttc aaccaaaacc accctgaaag cacagcagaa ttcaatgatt  1320
ctgactccgg catttcacta aacacaagtc ccagtgtggc atcaccagaa cactcagtgg  1380
aatcttccag ctatggagac acactacttg gcctcagtga ttctgaagtg gaagagctag  1440
atagtgcccc tggaagtgtc aaacagaatg gtcctaaaac accagtacat cttctggggg  1500
atatggtaca acccttgtca ccatctcagg ggcagagcac tcacgtgcat gatgcccaat  1560
gtgagaacac accagagaaa gaattgcctg taagtctcga ggaagatgcc aaaaacatta  1620
agaagggccc agcgccattc tacccactcg aagacgggac cgccggcgag cagctgcaca  1680
aagccatgaa gcgctacgcc ctggtgcccg gcaccatcgc ctttaccgac gcacatatcg  1740
aggtggacat tacctacgcc gagtacttcg agatgagcgt tcggctggca gaagctatga  1800
agcgctatgg gctgaataca aaccatcgga tcgtggtgtg cagcgagaat agcttgcagt  1860
tcttcatgcc cgtgttgggt gccctgttca tcggtgtggc tgtggcccca gctaacgaca  1920
tctacaacga gcgcgagctg ctgaacagca tgggcatcag ccagcccacc gtcgtattcg  1980
```

```
tgagcaagaa agggctgcaa aagatcctca acgtgcaaaa gaagctaccg atcatacaaa      2040
agatcatcat catggatagc aagaccgact accagggctt ccaaagcatg tacaccttcg      2100
tgacttccca tttgccaccc ggcttcaacg agtacgactt cgtgcccgag agcttcgacc      2160
gggacaaaac catcgccctg atcatgaaca gtagtggcag taccggattg cccaagggcg      2220
tagccctacc gcaccgcacc gcttgtgtcc gattcagtca tgcccgcgac cccatcttcg      2280
gcaaccagat catccccgac accgctatcc tcagcgtggt gccatttcac cacgcttcg      2340 gcatgttcac cacgctgggc tacttgatct gcggctttcg ggtcgtgctc atgtaccgct      2400
tcgaggagga gctattcttg cgcagcttgc aagactataa gattcaatct gccctgctgg      2460
tgcccacact atttagcttc ttcgctaaga gcactctcat cgacaagtac gacctaagca      2520
acttgcacga gatcgccagc ggcgggcgc cgctcagcaa ggaggtaggt gaggccgtgg      2580
ccaaacgctt ccacctacca ggcatccgcc agggctacgg cctgacagaa acaaccagcg      2640
ccattctgat cacccccgaa ggggacgaca agcctggcgc agtaggcaag gtggtgccct      2700
tcttcgaggc taaggtggtg acttggaca ccggtaagac actgggtgtg aaccagcgcg      2760
gcgagctgtg cgtccgtggc cccatgatca tgagcggcta cgttaacaac cccgaggcta      2820
caaacgctct catcgacaag gacggctggc tgcacacgcg cgacatcgcc tactgggacg      2880
aggacgagca cttcttcatc gtggaccggc tgaagagcct gatcaaatac aagggctacc      2940
aggtagcccc agccgaactg gagagcatcc tgctgcaaca ccccaacatc ttcgacgccg      3000
gggtcgccgg cctgcccgac gacgatgccg gcgagctgcc cgccgcagtc gtcgtgctgg      3060
aacacggtaa aaccatgacc gagaaggaga tcgtggacta tgtggccagc caggttacaa      3120
ccgccaagaa gctgcgcggt ggtgttgtgt tcgtggacga ggtgcctaaa ggactgaccg      3180
gcaagttgga cgcccgcaag atccgcgaga ttctcattaa ggccaagaag ggcggcaaga      3240
tcgccgtgga ctacaaggat gacgatgaca agtaatagct agc                       3283
```

<210> SEQ ID NO 13
<211> LENGTH: 2350
<212> TYPE: DNA
<213> ORGANISM: Artificial
<220> FEATURE:
<223> OTHER INFORMATION: 3xARE-TKbasal-OKD48-Venus

<400> SEQUENCE: 13

```
actagtggaa atgacattgc taatggtgac aaagcaactt ttctagtgga aatgacattg       60
ctaatggtga caaagcaact tttctagtgg aaatgacatt gctaatggtg acaaagcaac      120
ttttctagag gccccgccca gcgtcttgtc attggcgaat cgaacacgc agatgcagtc      180 ggggcggcgc ggtccgaggt ccacttcgca tattaaggtg acgcgtgtgg cctcgaacac      240
cgagcgaccc tgcagcgacc cgcttaacag cgtcaacagc gaagcttcta ggtaccatga      300
tggacttgga gctgccgccg ccgggactcc cgtcccagca ggacatggat ttgattgaca      360
tactttggag gcaagatata gatcttggag taagtcgaga agtatttgac ttcagtcagc      420
gacggaaaga gtatgagctg gaaaaacaga aaaaacttga aaaggaaaga caagaacaac      480
tccaaaagga gcaagagaaa gcctttttcg ctcagttaca actagatgaa gagacaggtg      540
aatttctccc aattcagcca gcccagcaca tccagtcaga aaccagtgga tctgccaact      600
actcccaggt tgcccacatt cccaaatcag atgctttgta ctttgatgac tgcatgcagc      660
ttttggcgca gacattcccg tttgtagatg acaatgaggt ttcttcggct acgtttcagt      720
```

```
cacttgttcc tgatattccc ggtcacatcg agagcccagt cttcattgct actaatcagg    780
ctcagtcacc tgaaacttct gttgctcagg tagcccctgt tgatttagac ggtatgcaac    840
aggacattga gcaagtttgg gaggagctat tatccattcc tgagttacag tgtcttaata    900
ttgaaaatga caagctggtt gagactacca tggttccaag tccagaagcc aaactgacag    960
aagttgacaa ttatcatttt tactcatcta taccctcaat ggaaaaagaa gtaggtaact   1020
gtagtccaca ttttcttaat gcttttgagg attccttcag cagcatcctc tccacagaag   1080
accccaacca gttgacagtg aactcattaa attcagatgc cacagtcaac acagattttg   1140
gtgatgaatt ttattctgct ttcatagctg agcccagtat cagcaacagc atgccctcac   1200
ctgctacttt aagccattca ctctctgaac ttctaaatgg gcccattgat gtttctgatc   1260
tatcactttg caaagctttc aaccaaaacc accctgaaag cacagcagaa ttcaatgatt   1320
ctgactccgg catttcacta aacacaagtc ccagtgtggc atcaccagaa cactcagtgg   1380
aatcttccag ctatggagac acactacttg gcctcagtga ttctgaagtg aagagctag    1440 atagtgcccc tggaagtgtc aaacagaatg gtcctaaaac accagtacat tcttctgggg   1500
atatggtaca acccttgtca ccatctcagg ggcagagcac tcacgtgcat gatgcccaat   1560
gtgagaacac accagagaaa gaattgcctg taagtctcga ggtgagcaag ggcgaggagc   1620
tgttcaccgg ggtggtgccc atcctggtcg agctggacgg cgacgtaaac ggccacaagt   1680
tcagcgtgtc cggcgagggc gagggcgatg ccacctacgg caagctgacc ctgaagctga   1740
tctgcaccac cggcaagctg cccgtgccct ggcccaccct cgtgaccacc ctgggctacg   1800
gcctgcagtg cttcgcccgc taccccgacc acatgaagca gcacgacttc ttcaagtccg   1860
ccatgcccga aggctacgtc caggagcgca ccatcttctt caaggacgac ggcaactaca   1920
agacccgcgc cgaggtgaag ttcgagggcg acaccctggt gaaccgcatc gagctgaagg   1980
gcatcgactt caaggaggac ggcaacatcc tggggcacaa gctggagtac aactacaaca   2040
gccacaacgt ctatatcacc gccgacaagc agaagaacgg catcaaggcc aacttcaaga   2100
tccgccacaa catcgaggac ggcggcgtgc agctcgccga ccactaccag cagaacaccc   2160
ccatcggcga cggccccgtg ttgctgcccg acaaccacta cctgagctac cagtccgccc   2220
tgagcaaaga ccccaacgag aagcgcgatc acatggtcct gctggagttc gtgaccgccg   2280
ccgggatcac tctcggcatg gacgagctgt acaaggacta caaggatgac gatgacaagt   2340
aatagctagc                                                          2350

<210> SEQ ID NO 14
<211> LENGTH: 53
<212> TYPE: DNA
<213> ORGANISM: Mus musculus

<400> SEQUENCE: 14
actagtacta gtggaaatga cattgctaat ggtgacaaag caacttttct aga           53

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
atcaccagaa cactcagtgg                                                20
```

```
<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
actcggcgta ggtaatgtcc                                              20
```